(12) United States Patent
Mostafavi

(10) Patent No.: US 8,200,315 B2
(45) Date of Patent: *Jun. 12, 2012

(54) PATIENT VISUAL INSTRUCTION TECHNIQUES FOR SYNCHRONIZING BREATHING WITH A MEDICAL PROCEDURE

(75) Inventor: Hassan Mostafavi, Los Altos, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/843,764

(22) Filed: Jul. 26, 2010

(65) Prior Publication Data

US 2010/0289821 A1 Nov. 18, 2010

Related U.S. Application Data

(63) Continuation of application No. 10/957,009, filed on Sep. 30, 2004, now Pat. No. 7,769,430.

(51) Int. Cl.
*A61B 5/00* (2006.01)

(52) U.S. Cl. ........................................ 600/428; 600/407

(58) Field of Classification Search .................. 600/407, 600/425, 427, 428
See application file for complete search history.

(56) References Cited

U.S. PATENT DOCUMENTS

| | | |
|---|---|---|
| 3,861,807 A | 1/1975 | Lescrenier |
| 3,871,360 A | 3/1975 | Van Horn et al. |
| 3,952,201 A | 4/1976 | Hounsfield |
| 4,031,884 A | 6/1977 | Henzel |
| 4,262,306 A | 4/1981 | Renner |
| 4,463,425 A | 7/1984 | Hirano et al. |
| 4,710,717 A | 12/1987 | Pele et al. |
| 4,804,261 A | 2/1989 | Kirschen |
| 4,853,771 A | 8/1989 | Witriol et al. |
| 4,895,160 A | 1/1990 | Reents |
| 4,971,065 A | 11/1990 | Pearce |
| 4,994,965 A | 2/1991 | Crawford et al. |
| 5,080,100 A | 1/1992 | Trotel |
| 5,271,055 A | 12/1993 | Hsieh et al. |
| 5,279,309 A | 1/1994 | Taylor et al. |
| 5,295,483 A | 3/1994 | Nowacki et al. |
| 5,315,630 A | 5/1994 | Sturm et al. |

(Continued)

FOREIGN PATENT DOCUMENTS

DE 4341324 6/1995

(Continued)

OTHER PUBLICATIONS

Non-Final Office Action dated Sep. 21, 2010 for U.S. Appl. No. 12/716,232.

(Continued)

*Primary Examiner* — Jacqueline Cheng
(74) *Attorney, Agent, or Firm* — Vista IP Law Group, LLP

(57) ABSTRACT

A method of prompting a patient includes informing a patient a relationship between a result of an activity being performed by the patient and a first target result to be achieved by the activity. A method of prompting a patient includes informing a patient a relationship between a time and a target result to be achieved by an activity. A method of prompting a patient includes informing a patient a relationship between a position of a portion of the patient and a first target position for the portion.

44 Claims, 6 Drawing Sheets

U.S. PATENT DOCUMENTS

| | | | |
|---|---|---|---|
| 5,363,844 A | 11/1994 | Riederer et al. | |
| 5,389,101 A | 2/1995 | Heilbrun et al. | |
| 5,394,875 A | 3/1995 | Lewis et al. | |
| 5,414,459 A | 5/1995 | Bullwinkel | |
| 5,446,548 A | 8/1995 | Gerig et al. | |
| 5,482,042 A | 1/1996 | Fujita | |
| 5,506,705 A | 4/1996 | Yamamoto et al. | |
| 5,513,646 A | 5/1996 | Lehrman et al. | |
| 5,538,494 A | 7/1996 | Matsuda | |
| 5,565,777 A | 10/1996 | Kanayama et al. | |
| 5,582,182 A | 12/1996 | Hillsman | |
| 5,588,430 A | 12/1996 | Bova et al. | |
| 5,603,318 A | 2/1997 | Heilbrun et al. | |
| 5,619,995 A | 4/1997 | Lobodzinski | |
| 5,622,187 A | 4/1997 | Carol | |
| 5,638,819 A | 6/1997 | Manwaring et al. | |
| 5,662,111 A | 9/1997 | Cosman | |
| 5,662,112 A | 9/1997 | Heid | |
| 5,714,884 A | 2/1998 | Hoshino | |
| 5,727,554 A | 3/1998 | Kalend et al. | |
| 5,764,723 A | 6/1998 | Weinberger et al. | |
| 5,771,310 A | 6/1998 | Vannah | |
| 5,784,431 A | 7/1998 | Kalend et al. | |
| 5,794,621 A | 8/1998 | Hogan et al. | |
| 5,806,116 A | 9/1998 | Oliver et al. | |
| 5,820,553 A | 10/1998 | Hughes | |
| 5,823,192 A | 10/1998 | Kalend et al. | |
| 5,825,563 A | 10/1998 | Anand | |
| 5,836,954 A | 11/1998 | Heilbrun et al. | |
| 5,861,865 A | 1/1999 | Anand et al. | |
| 5,906,202 A | 5/1999 | Schuster et al. | |
| 5,912,656 A | 6/1999 | Tham et al. | |
| 5,954,647 A | 9/1999 | Bova et al. | |
| 5,993,397 A | 11/1999 | Branson | |
| 5,997,439 A | 12/1999 | Ohsuga et al. | |
| 6,076,005 A | 6/2000 | Sontag et al. | |
| 6,138,302 A | 10/2000 | Sashin et al. | |
| 6,144,874 A | 11/2000 | Du | |
| 6,144,875 A | 11/2000 | Schweikard et al. | |
| 6,146,390 A | 11/2000 | Heilbrun et al. | |
| 6,165,181 A | 12/2000 | Heilbrun et al. | |
| 6,185,445 B1 | 2/2001 | Knuttel | |
| 6,185,446 B1 | 2/2001 | Carlsen | |
| 6,198,959 B1 | 3/2001 | Wang | |
| 6,272,368 B1 | 8/2001 | Alexandrescu | |
| 6,292,305 B1 | 9/2001 | Sakuma et al. | |
| 6,296,613 B1 | 10/2001 | Emmenegger et al. | |
| 6,300,974 B1 | 10/2001 | Viala et al. | |
| 6,307,914 B1 | 10/2001 | Kunieda et al. | |
| 6,348,058 B1 | 2/2002 | Melkent et al. | |
| 6,370,217 B1 | 4/2002 | Hu et al. | |
| 6,405,072 B1 | 6/2002 | Cosman | |
| 6,434,507 B1 | 8/2002 | Clayton et al. | |
| 6,473,635 B1 | 10/2002 | Rasche | |
| 6,501,981 B1 | 12/2002 | Schweikard et al. | |
| 6,527,443 B1 | 3/2003 | Vilsmeier et al. | |
| 6,611,617 B1 | 8/2003 | Crampton | |
| 6,621,889 B1 | 9/2003 | Mostafavi | |
| 6,665,370 B2 | 12/2003 | Bruder et al. | |
| 6,724,930 B1 | 4/2004 | Kosaka et al. | |
| 7,182,083 B2* | 2/2007 | Yanof et al. | 128/204.23 |
| 7,778,691 B2* | 8/2010 | Zhang et al. | 600/427 |
| 2002/0023652 A1 | 2/2002 | Riaziat et al. | |
| 2003/0007593 A1 | 1/2003 | Heuscher et al. | |
| 2003/0063292 A1 | 4/2003 | Mostafavi | |
| 2003/0072419 A1 | 4/2003 | Bruder et al. | |
| 2003/0188757 A1 | 10/2003 | Yanof et al. | |
| 2003/0190010 A1 | 10/2003 | Tsujii | |
| 2003/0210812 A1 | 11/2003 | Khamene et al. | |
| 2004/0005088 A1 | 1/2004 | Jeung et al. | |
| 2004/0030235 A1* | 2/2004 | Sasaki et al. | 600/413 |
| 2004/0071337 A1 | 4/2004 | Jeung et al. | |
| 2004/0082853 A1 | 4/2004 | Sasaki et al. | |
| 2004/0116804 A1 | 6/2004 | Mostafavi | |
| 2004/0218719 A1 | 11/2004 | Brown et al. | |
| 2004/0254773 A1 | 12/2004 | Zhang et al. | |
| 2005/0119560 A1 | 6/2005 | Mostafavi | |
| 2005/0283068 A1 | 12/2005 | Zuccolotto et al. | |
| 2006/0074286 A1 | 4/2006 | Miller et al. | |
| 2006/0074305 A1 | 4/2006 | Mostafavi | |
| 2006/0079763 A1 | 4/2006 | Jeung et al. | |
| 2006/0129044 A1* | 6/2006 | Le Corre | 600/428 |

FOREIGN PATENT DOCUMENTS

| | | |
|---|---|---|
| DE | 19856467 | 5/2000 |
| EP | 1050272 | 11/2000 |
| FI | 79458 | 9/1989 |
| JP | 2000 262511 | 9/2000 |
| JP | 2000 325339 | 11/2000 |
| JP | 2002 090118 | 3/2002 |
| JP | 2004-000412 A | 1/2004 |
| WO | WO 9816151 | 4/1998 |
| WO | WO 9838908 | 9/1998 |
| WO | WO 9852635 | 11/1998 |
| WO | WO 9830977 | 7/1999 |
| WO | WO 0024333 | 5/2000 |
| WO | WO 02085455 | 10/2002 |
| WO | 03/003796 A1 | 1/2003 |
| WO | WO 03003796 | 1/2003 |

OTHER PUBLICATIONS

Final Office Action dated Apr. 13, 2011 for U.S. Appl. No. 12/716,232.

Adams, W.B. et al. "Correlator Compensation Requirements for Passive Time-Delay Estimation with Moving Source or Receivers" IEEE Transactions on Acoustics, Speech and Signal Processing (Apr. 1980) ASSP 28(2):158-168.

Ahlström, K.H. et al "Pulmonary MR Angiography with Ultrasmall Superparamagnetic Iron Oxide Particles as a Blood Pool Agent and a Navigator Echo for Respiratory Gating: Pilot Study" Radiology (Jun. 1999) 211(3):865-869.

Axel, L. et al. "Respiratory Effects in Two-Dimensional Fourier Transform MR Imaging" Radiology (Sep. 1986) 160(3):795-801.

Balter, J.M. et al. "Uncertainties in CT-Based Radiation Therapy Treatment Planning Associated with Patient Breathing" Int. J. Radiation Oncology Biol. Phys. (Aug. 1, 1996) 36(1):167-174.

Bankman, I.N. et al. "Optimal Detection, Classification, and Superposition Resolution in Neural Waveform Recordings" IEEE Transactions on Biomedical Engineering (Aug. 1993) 40(8):836-841.

Baroni, G. and G. Ferrigno "Real-time Motion Analysis for Definition and Control of Patient Position in Radiotherapy" Proc. SPIE Medical Imaging 1996: Physiology and Function from Multidimensional Images (Apr. 1996) 2709:506-515.

Bellenger, N.G. et al. "Left Ventricular Quantification in Heart Failure by Cardiovascular MR Using Prospective Respiratory Navigator Gating: Comparison with Breath-Hold Acquisition" Journal of Magnetic Resonance Imaging (Apr. 2000) 11(4):411-417.

Cho.K. et al. "Development of Respiratory Gated Myocardial SPECT System" J. Nuci. Cardiol. (Jan./Feb. 1999) 6(1):20-28.

Danias, P.G. et al. "Prospective Navigator Correction of Image Position for Coronary MR Angiography" Radiology (Jun. 1997) 203:733-736.

Davies, S.C. et al. "Ultrasound Quantitation of Respiratory Organ Motion in the Upper Abdomen" Br. J. Radiol. (Nov. 1994) 67(803):1096-1102.

Du, Y.P. "Prospective navigator gating with a dual acceptance window technique to reduce respiratory motion artifacts in 3D MR coronary angiography" Int'l J. Cardiovascular Imaging (2003) 19:157-162.

Du, Y.P. et al. "A comparison of prospective and retrospective respiratory navigator gating in 3D MR coronary angiography" Int'l J. Cardiovascular Imaging (2001) 17:287-294.

Ehman, R.L. et al. "Magnetic Resonance Imaging with Respiratory Gating: Techniques and Advantages" AJR (Dec. 1984) 143:1175-1182.

Fee, M.S. et al. "Automatic Sorting of Multiple Unit neuronal Signals in the Presence of Anisotropic and non-Gaussian Variability" J. Neuroscience Methods (1996) 69:175-188.

Felblinger, J. et al. "Effects of physiologic motion of the human brain upon quantitative 1H-MRS: analysis and correction by retrogating" NMR in Biomedicine (1998) 11:107-114.

Fishbein, K.W. et al. "The lever-coil: a simple, inexpensive sensor for respiratory and cardiac in MRI experiments" Magnetic Resonance Imaging (2001) 19:881-889.

Frölich, H. et al. "A Simple Device for Breath-Level Monitoring During CT" Radiology (Jul. 1985) 156(1):235.

Gerig, L.H. et al. "The Development and Clinical Application of a Patient Position Monitoring System" Proc. SPIE Videometrics III (Oct. 1994) 2350:59-72.

Haacke, E.M. and G.W. Lenz " Improving MR Image Quality in the Presence of Motion by Using Rephasing Gradients" AJR (Jun. 1987) 148:1251-1258.

Hanley, J. et al. "Deep Inspiration Breath-Hold Technique for Lung Tumors: The Potential Value of Target Immobilization and Reduced Lung Density in Dose Escalation" Int. J. Radiation Oncology biol. Phys. (Oct. 1, 1999) 45(3):603-611.

Henkelman, R.M. and K. Mah "How Important is Breathing in Radiation Therapy of the Thorax?" Int. J. Radiation Oncology Biol. Phys. (Nov. 1982) 8(11):2005-2010.

Hofman, M.B.M. et al. "MRI of Coronary Arteries: 2D Breath-Hold vs. 3D Respiratory-Gated Acquisition" J. Computer Assisted Tomography (Jan./Feb. 1995) 19(1):56-62.

Huber, A. et al. "Navigator Echo-Based Respiratory Gating for Three-Dimensional MR Coronary Angiography: Results from Healthy Volunteers and Patients with Proximal Coronary Artery Stenoses" AJR (Jul. 1999) 173:95-101.

Iwasawa, T. et al. "Normal In-Plane Respiratory Motion of the Bilateral Hemidiaphragms Evaluated by Sequentially Subtracted Fast Magnetic Resonance Images" Journal of Thoracic Imaging (1999) 14(2):130-134.

Johnson, L.S. et al. "Initial Clinical Experience with a Video-Based Patient Positioning System" Int. J. Radiation Oncology Biol. Phys. (Aug. 1, 1999) 45(1):205-213.

Jolesz, F. "Image-guided Procedures and the Operating Room of the Future" Radiology (May 1997) 204:601-612.

Josefsson, T. et al. "A Flexible High-Precision Video System for Digital Recording of Motor Acts Through Lightweight Reflex Markers" Computer Methods & Programs in Biomedicine (1996) 49:119-129.

Kachelriess, M. and W.A. Kalender "Electrocardiogram-Correlated Image Reconstruction from Subsecond Spiral Computed Tomography Scans of the Heart" Med. Phys. (Dec. 1998) 25(12):2417-2431.

Keatley, E. et al "Computer Automated Diaphragm Motion Quantification in a Fluoroscopic Movie" Proceedings of the 22nd Annual International Conference of the IEEE Engineering in Medicine and Biology Society, Chicago, IL (Jul. 23-28, 2000) 3:1749-1751.

Kim, W.S., et al. "Extraction of Cardiac and Respiratory Motion Cycles by Use of Projection Data and its Applications NMR Imaging" Magnetic Resonance in Medicine (1990) 13:25-37.

Korin, H.W. et al. "Respiratory Kinematics for the Upper Abdominal Organs: A Quantitative Study" Magnetic Resonance in Medicine (Jan. 1992) 23(1):172-178.

Kubo, H.D. and L. Wang "Compatibility of Varian 2100C Gated Operations with Enhanced Dynamic Wedge and IMRT Dose Delivery" Med. Phys. (Aug. 2000) 27(8):1732-1738.

Kubo, H.D. et al. " Respiration Gated Radiotherapy Treatment: A Technical Study" Phys. Med. Biol. (1996) 41:83-91.

Kubo, H.D. et al. "Breathing-Synchronized Radiotherapy Program at the University of California Davis Cancer Center" Med. Phys. (Feb. 2000) 27(2):346-353.

Kubo, H.D. et al. "Potential and Role of a Prototype Amorphous Silicon Array Electronic Portal Imaging Device In Breathing Synchronized Radiotherapy" Med. Phys. (Nov. 1999) 26(11):2410-2414.

Kutcher, G.J. et al. " Control, Correction, and Modeling of Setup Errors and Organ Motion" Seminars in Radiation Oncology. (Apr. 1995) 5(3):134-145.

Lee, M.W. and I. Cohen "Human Body Tracking with Auxiliary Measurements" IEEE International Workshop on Analysis and Modeling of Faces and Gestures (2003) 8 pgs., located at http://iris.usc.edu/~icohen/projects/human/body/index.htm.

Leiberman, J.M. et al. " Gated Magnetic Resonance Imaging of the Normal Diseased Heart" Radiology (Aug. 1984) 152:465-470.

Lethimonnier, F. et al. "Three-Dimensional Coronary Artery MR Imaging Using Prospective Real-Time Respiratory Navigator and Linear Phase Shift Processing: Comparison with Conventional Coronary Angiography" Magnetic Resonance Imaging (1999) 17(8):1111-1120.

Lewis, C.E. et al. "Comparison of Respiratory Triggering and Gating Techniques for the Removal of Respiratory Artifacts in MR Imaging" Radiology (Sep. 1986) 160(3):803-810.

Li, D. et al. "Coronary Arteries: Three-Dimensional MR Imaging with Retrospective Respiratory Gating" Radiology (Dec. 1996) 201(3):857-863.

Lopresti, B.J. et al. "Implementation and Performance of an Optical Motion Tracking System for High Resolution Brain PET Imaging" IEEE Transactions on Nuclear Science (Dec. 1999) 46(6):2059-2067.

Luker, G.D. et al. "Ghosting of Pulmonary Nodules with Respiratory Motion: Comparison of Helical and Conventional CT Using and In Vitro Pediatric Model" AJR (Nov. 1996) 167:1189-1193.

Mageras, G. et al. "Initial Clinical Evaluation of a Respiratory Gating Radiotherapy System" in 22nd Annual EMBS International Conference, Chicago, IL (Jul. 23-28, 2000) pp. 2124-2127.

Mageras, G.S. "Interventional Strategies for Reducing Respiratory-Induced Motion in External Beam Therapy" The Use of Computers in Radiation Therapy, XIIIth International Conference, Heidelberg, Germany (May 22-25, 2000) pp. 514-516.

Mageras, G.S. et al. "Respiratory Motion-Induced Treatment Uncertainties" Patras Medical Physics 99—VI International Conference on Medical Physics, Patras (Greece) (Sep. 1-4, 1999) pp. 33-39.

Mah, D. et al. "Technical Aspects of the Deep Inspiration Breath-Hold Technique in the Treatment of Thoracic Cancer" Int. J. Radiation Oncology Biol. Phys. (Nov. 1, 2000) 48(1):1175-1185.

Mah, K. and R.M. Henkelman "Time Varying Dose Due to Respiratory Motion During Radiation Therapy of the Thorax"; Proceedings of the Eighth Int'l Conference on the Use of Computers in Radiation Therapy, Toronto, Canada (Jul. 9-12, 1984) pp. 294-298.

Malone, S. et al. "Respiratory-Induced Prostate Motion: Quantification and Characterization" Int. J. Radiation Oncology Biol. Phys. (Aug. 2000) 48:105-109.

Manke, D. et al. "Model Evaluation and Calibration for Prospective Respiratory Motion Correction in Coronary MR Angiography Based on 3-D Image Registration" IEEE Transactions on Medical Imaging (Sep. 2002) 21(9):1132-1141.

Manke, D. et al. "Respiratory Motion in Coronary Magnetic Resonance Angiography: A Comparison of Different Motion Models" J. Magnetic Resonance Imaging (2202) 14:661-671.

McConnell, M.V. et al. "Comparison of Respiratory Suppression Methods and Navigator Locations for MR Coronary Angiography" AJR (May 1997) 168:1369-1375.

McConnell, M.V. et al. "Prospective Adaptive Navigator Correction for Breath-Hold MR Coronary Angiography" MRM (1997) 37:148-152.

Moerland, M.A. et al. "The Influence of Respiration Induced Motion of the Kidneys on the Accuracy of Radiotherapy Treatment Planning, a Magnetic Resonance Imaging Study" Radiotherapy and Oncology (1994) 30:150-154.

Mori, M. et al. "Accurate Contiguous Sections Without Breath-Holding on Chest CT: Value of Respiratory Gating and Ultrafast CT" AJR (May 1994) 162:057-1062.

Nevatia, R. et al. "Human Body Tacking with Articulated Human Body Model" (Nov. 2002) pp. 1-3 located at http://www.scf.usc.edu/~munlee/humanBodyTrk.html.

Nikolaou, K. et al. " Navigator Echo-Based Respiratory Gating for Three-Dimensional MR Coronary Angiography: Reduction of Scan Time Using a Slice Interpolation Technique" J. Computer Assisted Tomography (2001) 25(3):378-387.

Ohara, K. et al. "Irradiation Synchronized with Respiration Gate" Int. J. Radiation Oncology Biol. Phys. (Oct. 1989) 17(4):853-857.

Oshinski, J.N. et al. "Two-Dimensional Coronary MR Angiography Without Breath-Holding" Radiology (Dec. 1996) 201(3):737-743.

Paradis, A.L. et al. "Detection of Periodic Signals in Brain Echo-Planar Functional Images" Proceedings of the 18th Annual International Conference of the IEEE Engineering in Medicine and Biology Society, Amsterdam, The Netherlands (1996) pp. 696-697.

Peltola, S. "Gated Radiotherapy to Compensate for Patient Breathing" Proceedings of the Eleventh Varian Users Meeting, Marco Island, Florida (May 11-13, 1986) 3 pgs.

Plein, S. et al. "Three-Dimensional Coronary MR Angiography Performed with Subject-Specific Cardiac Acquisition Windows and Motion-Adapted Respiratory Gating" AJR (Feb. 2003) 180:505-512.

Post, J.C. et al. "Three-Dimensional Respiratory-Gated MR Angiography of Coronary Arteries: Comparison with Conventional Coronary Angiography" AJR (Jun. 1996) 166:1399-1404.

Ramsey, C.R. et al. "A Comparison of Beam Characteristics for Gated and Nongated Clinical X-Ray Beams" Med. Phys. (Oct. 1999) 26(10):2086-2091.

Ramsey, C.R. et al. "Clinical Efficacy of Respiratory Gated Conformal Radiation Therapy" Medical Dosimetry (1999) 24(2):115-119.

Regenfus, M. et al. "Comparison of Contrast-Enhanced Breath-Hold and Free-Breathing Respiratory-Gated Imaging in Three-Dimensional Magnetic Resonance Coronary Angiography" Am. J. Cardiology (Oct. 1, 2002) 90:725-730.

Ritchie, C.J. et al. "Predictive Respiratory Gating: A New Method to Reduce Motion Artifacts on CT Scans" Radiology (Mar. 1994) 190(3):847-852.

Robinson, T.E. et al. "Standardized High-Resolution CT of the Lung Using a Spirometer-Triggered Electron Beam CT Scanner" AJR (Jun. 1999) 172:1636-1638.

Rogus, R.D. et al. "Accuracy of a Photogrammetry-Based Patient Positioning and Monitoring System for Radiation Therapy" Med. Phys. (May 1999) 26(5):721-728.

Rosenzweig, K.E. et al. "The Deep Inspiration Breath-Hold Technique in the Treatment of Inoperable Non Small Cell Lung Cancer" Int. J. Radiation Oncology Biol. Phys. (Aug. 1, 2000) 48(1):81-87.

Ross, C.S et al. "Analysis of Movement of Intrathoracic Neoplasms Using Ultrafast Computerized Tomography" Int. J. Radiation Oncology Biol. Phys. (Mar. 1990) 18(3):671-677.

Runge, V.M. et al. "Respiratory Gating in Magnetic Resonance Imaging at 0.5 Tesla" Radiology (May 1984) 151 (2):521-523.

Sachs, T.S. et al. "Real-Time Motion Detection in Spiral MRI Using Navigators" Magnetic Resonance in Medicine (Nov. 1994) 32(5):639-645.

Schär, M. et al. "the Impact of Spatial Resolution and Respiratory Motion on MR Imaging of Atherosclerotic Plaque" J. Magnetic Resonance Imaging (2003) 17:538-544.

Schwartz, L.H. et al. "Kidney Mobility During Respiration" Radiotherapy and Oncology. (1994) 32:84-86.

Shirato, H. et al. "Four-Dimensional Treatment Planning and Fluroscopic Real-Time Tumor Tracking Radiotherapy for Moving Rumor" Int. J. Radiation Oncology Biol. Phys. (Sep. 1, 2000) 48(2):435-442.

Sinkus, R. and P. Börnert "Motion Pattern Adapted Real-Time Respiratory Gating" Magnetic Resonance in Medicine (1999) 41:148-155.

Solberg, T.D. et al. "Feasibility of Gated IMRT" Proceedings of the 22nd annual International Conference of the IEEE Engineering in Medicine and Biology Society, Chicago, IL (Jul. 23-28, 2000) 4:2732-2734.

Spuentrup, E. et al. "Respiratory motion artifact suppression in diffusion-weighted MR imaging of the spine" Eur. Radiol. (2003) 13:330-336.

Suramo, I. et al. "Cranio-Caudal Movements of the Liver, Pancreas and Kidneys on Respiration" Acta Radiology Diagnosis (1984) 25(2):129-131.

Tada, T. et al. "Lung Cancer: Intermittent Irradiation Synchronized with Respiratory Motion-Results of a Pilot Study" Radiology (Jun. 1998) 207(3):779-783.

Thickman, D. et al. "Phase-Encoding Direction upon Magnetic Resonance Image Quality of the Heart" Magnetic Resonance in Medicine (1998) 6:390-396.

van Geuns, R.J.M. et al. "Magnetic Resonance Imaging of the Coronary Arteries: Clinical Results from Three Dimensional Evaluation of a Respiratory Gated Technique" Heart (Oct. 1999) 82(4):515-519.

Wang Y. et al. "Navigator-Echo-based Real-Time Respiratory Gating and Triggering for Reduction of Respiration Effects in Three-dimensional Coronary MR Angiography" Radiology (1996) 198:55-60.

Wang, Y. et al. "Respiratory Motion of the Heart: Kinematics and the Implications for the Spatial Resolution in Coronary Imaging" Magnetic Resonance in Medicine (1995) 33:713-719.

Weber, C. et al. "Correlation of 3D MR coronary angiography with selective coronary angiography: feasibility of the motion adapted gating technique" Eur. Radiol. (2002) 12:718-726.

Weiger, M. et al. "Motion-Adapted Gating Based on k-Space Weighting for Reduction of Respiratory Motion Artifacts" Magnetic Resonance in Medicine (Aug. 1997) 38(2):322-333.

Wiesmann, F. "High-Resolution MRI with Cardiac and Respiratory Gating Allows for Accurate in Vivo Atherosclerotic Plaque Visualization in Murine Aortic Arch" Magnetic Resonance in Medicine (2003) 50:69-74.

Wong, J.W. et al. "The Use of Active Breathing Control (ABC) to Reduce Margin for Breathing Motion" Int. J. Radiation Oncology Biol. Phys. (Jul. 1, 1999) 44(4):911-919.

Wood, M.L. and R.M. Henkelman "Suppression of respiratory motion artifacts in magnetic resonance imaging" Med. Phys. (Nov./Dec. 1996) 13(6):794-805.

Woodard, P.K. et al. "Detection of Coronary Stenoses on Source and Projection Images Using Three-Dimensional MR Angiography with Retrospective Respiratory Gating: Preliminary Experience" AJR (Apr. 1998) 170(4):883-888.

Worthley, S.G. et al. "Cardiac gated breath-hold back blood MRI of the coronary artery wall: An in vivo and ex vivo comparison" Int'l J. Cardiovascular Imaging (2001) 17:195-201.

Yamashita, Y. et al. "MR Imaging of Focal Lung Lesions: Elimination of Flow and Motion Artifacts by Breath-Hold ECG-Gated and Black-Blood Techniques on T2-Weighted Turbo SE and STIR Sequences" J. Magnetic Resonance Imaging (1999) 9:691-698.

Yorke, Ellen et al "Respiratory Gating of Sliding Window IMRT" Proceedings of the 22nd Annual International Conference of the IEEE Engineering in Medicine and Biology Society, Chicago, IL (Jul. 23-28, 2000) 3:2118-2121.

Yuan, Q. et al. "Cardiac-Respiratory Gating Method for Magnetic Resonance Imaging of the Heart" Magnetic Resonance in Medicine (Feb. 2000) 43:314-318.

Preliminary Search Brochure entitled "Kinematic Measurement Systems" by Qualisys printed Apr. 4, 1994.

http://en.wikipedia.org/wiki/Frogger, printed Dec. 2006.

International Search Report and Written Opinion dated Feb. 5, 2007 for PCT/US2005/034999.

Supplementary European Search Report dated Aug. 28, 2008 for EP05803610.

Notification of the First Office Action dated May 9, 2008 for CN200580039470.8.

Notification of the Second Office Action dated Oct. 31, 2008 for CN200580039470.8.

Notification of the Third Office Action dated Apr. 10, 2009 for CN200580039470.8.

Non Final Office Action dated Jan. 22, 2009 for U.S. Appl. No. 10/956,199.

Non Final Office Action dated Jan. 10, 2008 for U.S. Appl. No. 10/956,199.

Non Final Office Action dated Mar. 23, 2007 for U.S. Appl. No. 10/956,199.

Final Office Action dated Aug. 3, 2009 for U.S. Appl. No. 10/956,199.

Final Office Action dated Oct. 5, 2007 for U.S. Appl. No. 10/956,199.

Final Office Action dated Oct. 15, 2009 for U.S. Appl. No. 10/956,199.

Non Final Office Action dated Aug. 18, 2009 for U.S. Appl. No. 11/217,789.

Non Final Office Action dated Oct. 6, 2008 for U.S. Appl. No. 11/217,789.

Final Office Action dated Apr. 23, 2009 for U.S. Appl. No. 11/217,789.

Advisory Action dated Jul. 10, 2009 for U.S. Appl. No. 11/217,789.

Non Final Office Action dated Jan. 26, 2009 for U.S. Appl. No. 10/957,009.

Non Final Office Action dated Dec. 18, 2006 for U.S. Appl. No. 10/957,009.

Non Final Office Action dated Dec. 30, 2005 for U.S. Appl. No. 10/957,009.
Final Office Action dated Jul. 8, 2009 for U.S. Appl. No. 10/957,009.
Final Office Action dated Apr. 17, 2008 for U.S. Appl. No. 10/957,009.
Final Office Action dated Oct. 4, 2007 for U.S. Appl. No. 10/957,009.
Advisory Action dated Aug. 29, 2008 for U.S. Appl. No. 10/957,009.
Advisory Action dated Dec. 11, 2007 for U.S. Appl. No. 10/957,009.
Notice of Allowance dated Mar. 24, 2010 for U.S. Appl. No. 10/957,009.
Final Notice of Reasons for Refusal dated Mar. 22, 2012 for JP Patent Application No. 2007-534756.
English Translation of Final Notice of Reasons for Refusal dated Mar. 22, 2012 for JP Patent Application No. 2007-534756.

* cited by examiner

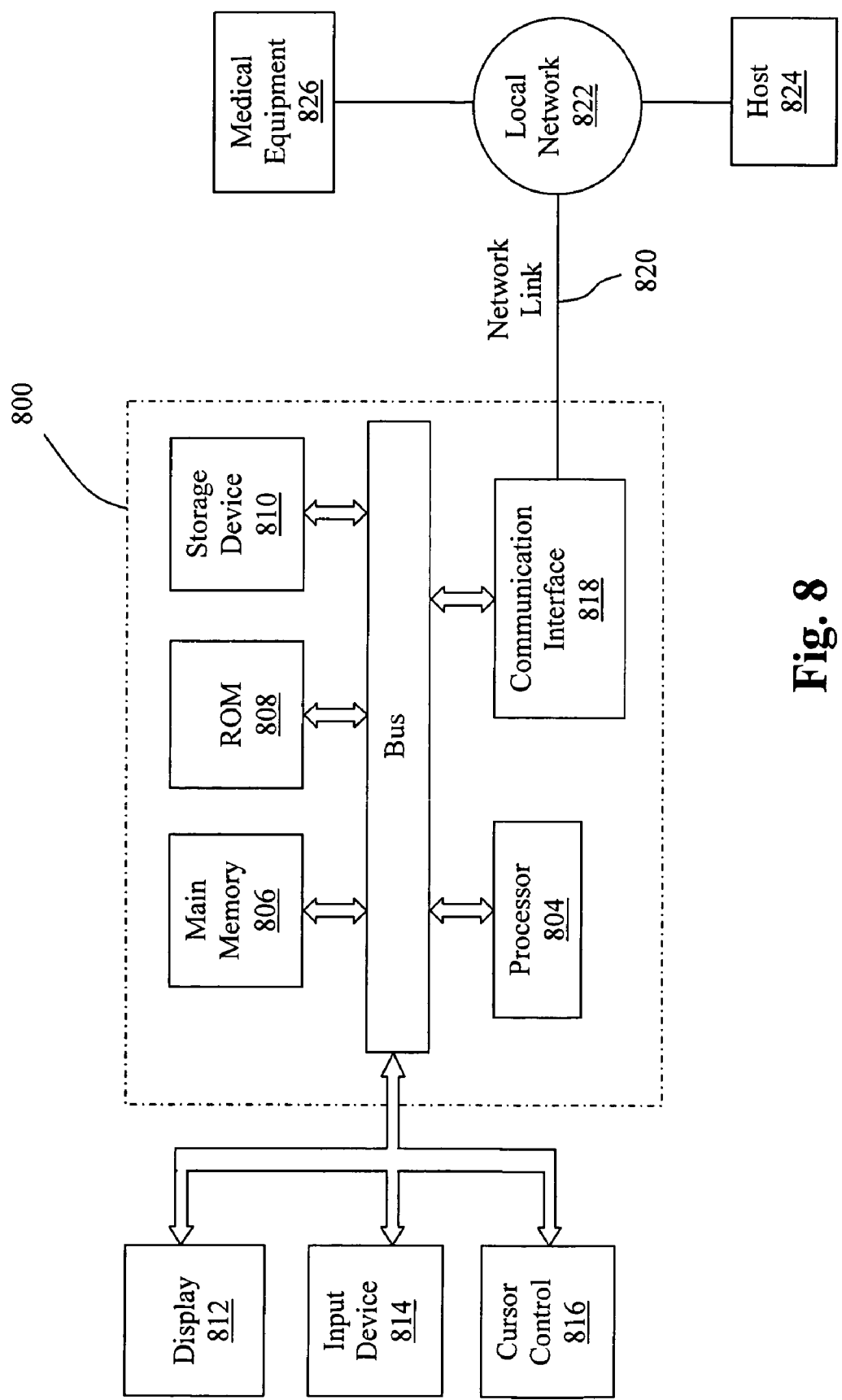

PATIENT VISUAL INSTRUCTION TECHNIQUES FOR SYNCHRONIZING BREATHING WITH A MEDICAL PROCEDURE

RELATED APPLICATION DATA

This application is a continuation of U.S. patent application Ser. No. 10/957,009, filed on Sep. 30, 2004, now U.S. Pat. No. 7,769,430, the entire disclosure of which is expressly incorporated by reference herein.

This application is related to U.S. patent application Ser. No. 10/956,199, entitled, "Patient Multimedia Display", abandoned, filed on Sep. 30, 2004, and U.S. patent application Ser. No. 09/893,122, filed Jun. 26, 2001, now U.S. Pat. No. 6,937,696, the entire disclosure of which is expressly incorporated by reference herein.

BACKGROUND OF THE INVENTION

1. Field of the Invention

This invention relates generally to systems and methods for prompting patient, and more specifically, to systems and methods for prompting patient to control patient movement.

2. Background of the Invention

Computed tomography is an imaging technique that has been widely used in the medical field. In a procedure for computed tomography, an x-ray source and a detector apparatus are positioned on opposite sides of a portion of a patient under examination. The x-ray source generates and directs a x-ray beam towards the patient, while the detector apparatus measures the x-ray absorption at a plurality of transmission paths defined by the x-ray beam during the process. The detector apparatus produces a voltage proportional to the intensity of incident x-rays, and the voltage is read and digitized for subsequent processing in a computer. By taking a plurality of readings from multiple angles around the patient, relatively massive amounts of data are thus accumulated. The accumulated data are then analyzed and processed for reconstruction of a matrix (visual or otherwise), which constitutes a depiction of a density function of a volume of the bodily region being examined. By considering one or more sections in the volume, a skilled diagnostician can often diagnose various bodily ailments such as tumors, blood clots, etc.

Computed tomography has found its principal application to examination of bodily structures or the like which are in a relatively stationary condition. However, currently available computed tomographic apparatus may not be able to generate tomographic images with sufficient quality or accuracy due to physiological movement of a patient. For example, beating of a human heart and breathing have been known to cause degradation of quality in CT images. U.S. Pat. No. 3,952,201 issued to Hounsfield, describes a system that compensates for a blurring of a radiograph due to heart motions by collecting image data of a patient at different angles while monitoring the patient's heart. The image data and the heart motion data are then correlated in a computer, and image data that was obtained when the heart's motion exceeded a threshold level is rejected. However, such method does not generate desirable CT images for a portion of a cardiac cycle when the heart's motion exceeds the threshold level.

Degradation of quality of CT images due to patient's breathing is more difficult to address than that associated with heart motion. Patients' breathing poses a unique problem to CT imaging that is different from heart motion. This is because the pattern and the period of a patient's breathing cycle is generally less consistent when compared to those of the patient's cardiac cycle. As such, while a particular phase of a cardiac cycle may be predicted with sufficient accuracy, a particular phase of a breathing cycle may not be as easily predicted or determined.

Furthermore, there has been an increased desire to visualize organ motion by viewing a sequence of CT images as a movie sequence. However, collecting a large quantity of CT image data sufficient for forming a video while considering breathing motion may take a much longer time. This may cause a patient who is confined within a gantry opening to feel uncomfortable and subject the patient to excessive radiation.

To reduce durations of CT image acquisition procedures, patient prompting techniques have been used to control patients' breathing during CT procedures. Such techniques involve sending an audio signal to instruct a patient to inhale, exhale, or hold breath. However, successful implementation of such techniques requires the audio signal be provided to the patient in a timely manner. If the signal is provided too early, the patient may perform a required physiological movement earlier than expected. On the other hand, if the signal is provided too late, the patient may not be able to perform the required physiological movement in time to meet the procedure's requirement. Also, different patients may have different reaction times—i.e., some patients may react faster in response to the audio signal, while others may react slower in response to the audio signal. As such, existing techniques for prompting a patient are difficult to implement, and may not provide satisfactory results due to different patients' reaction time.

For the foregoing, it would be desirable to have an improved method and system for prompting a patient in a medical procedure.

SUMMARY OF THE INVENTION

In accordance with some embodiments of the invention, a method of prompting a patient includes informing a patient a relationship between a result of an activity being performed by the patient, and a first target result to be achieved by the activity.

In accordance with other embodiments of the invention, a computer program product that includes a medium is provided. The medium includes a set of instructions, an execution of which causes a process to be performed, the process comprising informing a patient a relationship between a result of an activity being performed by the patient, and a first target result to be achieved by the activity.

In accordance with other embodiments of the invention, a system for prompting a patient includes means for informing a patient a relationship between a result of an activity being performed by the patient, and a first target result to be achieved by the activity.

In accordance with other embodiments of the invention, a user interface for prompting a patient includes a screen displaying graphics for informing a patient a relationship between a result of an activity being performed by the patient, and a first target result to be achieved by the activity.

In accordance with other embodiments of the invention, a method of prompting a patient includes informing a patient a relationship between a time and a target result to be achieved by an activity.

In accordance with other embodiments of the invention, a computer program product that includes a medium is provided. The medium includes a set of instructions, an execution of which causes a process to be performed, the process comprising informing a patient a relationship between a time and a target result to be achieved by an activity.

In accordance with other embodiments of the invention, a system for prompting a patient includes means for informing a patient a relationship between a time and a target result to be achieved by an activity.

In accordance with other embodiments of the invention, a user interface for prompting a patient includes a screen displaying graphics for informing a patient a relationship between a time and a target result to be achieved by an activity.

In accordance with other embodiments of the invention, a method of prompting a patient includes informing a patient a relationship between a position of a portion of the patient and a first target position for the portion.

In accordance with other embodiments of the invention, a computer program product that includes a medium is provided. The medium includes a set of instructions, an execution of which causes a process to be performed, the process comprising informing a patient a relationship between a position of a portion of the patient and a first target position for the portion.

In accordance with other embodiments of the invention, a system for prompting a patient includes means for informing a patient a relationship between a position of a portion of the patient and a first target position for the portion.

In accordance with other embodiments of the invention, a user interface for prompting a patient includes a screen displaying graphics for informing a patient a relationship between a position of a portion of the patient and a first target position for the portion.

Other aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how advantages and objects of the present invention are obtained, a more particular description of the present invention briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 8 is a block diagram that illustrates an embodiment of a computer system upon which embodiments of the invention may be implemented.

DETAILED DESCRIPTION OF THE PREFERRED EMBODIMENTS

Figure 1:
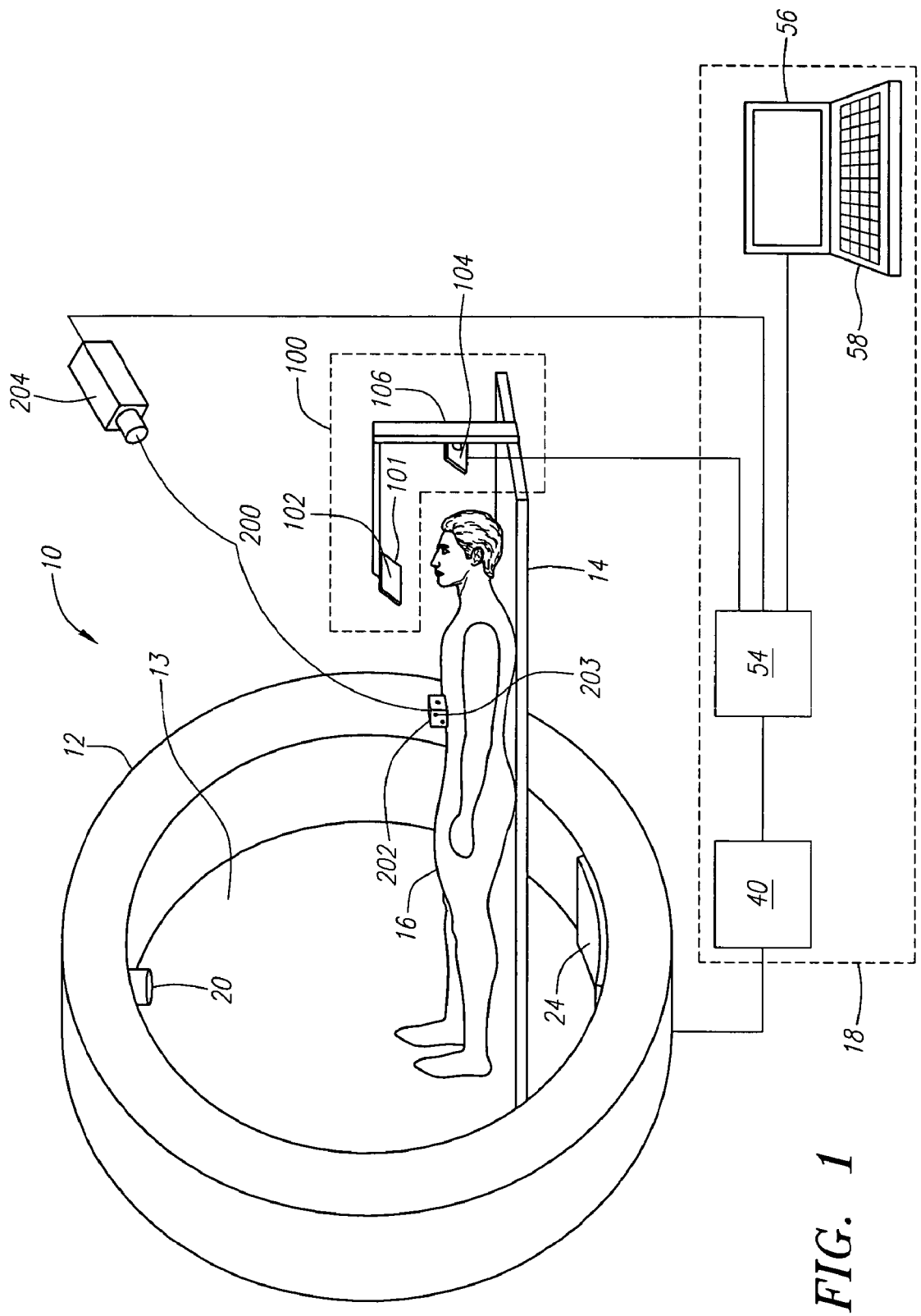
FIG. 1 illustrates a computed tomography system in which embodiments of the invention can be implemented.

Various embodiments of the present invention are described hereinafter with reference to the figures. It should be noted that the figures are not drawn to scale and elements of similar structures or functions are represented by like reference numerals throughout the figures. It should also be noted that the figures are only intended to facilitate the description of specific embodiments of the invention. They are not intended as an exhaustive description of the invention or as a limitation on the scope of the invention. Also, an aspect described in conjunction with a particular embodiment of the present invention is not necessarily limited to that embodiment and can be practiced in any other embodiments of the present invention. In addition, a means for performing a function may be used to perform another function, and a function may be performed by one or more means.

Computed Tomography Image Acquisition System

Referring now to the drawings, in which similar or corresponding parts are identified with the same reference numeral, FIG. 1 illustrates a computed tomography image acquisition system 10, in which embodiments of the present invention can be employed. The system 10 includes a gantry 12 having an opening (or bore) 13, a patient support 14 for supporting a patient 16, and a control system 18 for controlling an operation of the gantry 12. In other embodiments, instead of the ring configuration shown, the gantry 12 can have other configurations. For example, the gantry 12 can have a C-arm configuration, such as that used in the cone beam CT machines manufactured by Varian Medical Systems, Inc., in Palo Alto, Calif. The system 10 also includes an x-ray source 20 that projects a beam (which can be a cone beam, a fan beam, or the like) of x-rays towards a detector 24 on an opposite side of the gantry 12 while the patient 16 is positioned at least partially between the x-ray source 20 and the detector 24. The detector 24 has a plurality of sensor elements configured for sensing a x-ray that passes through the patient 16. Each sensor element generates an electrical signal representative of an intensity of the x-ray beam as it passes through the patient 16.

In the illustrated embodiment, the control system 18 includes a processor 54, such as a computer processor, coupled to a gantry rotation control 40 and a patient prompting device 100. The control system 18 may also include a monitor 56 for displaying data and an input device 58, such as a keyboard or a mouse, for inputting data. During a scan to acquire x-ray projection data (i.e., CT image data), the gantry 12 rotates about the patient 16. The rotation of the gantry 12 and the operation of the x-ray source 20 are controlled by the gantry rotation control 40, which provides power and timing signals to the x-ray source 20 and controls a rotational speed and position of the gantry 12 based on signals received from the processor 54. Although the control 40 is shown as a separate component from the gantry 12 and the processor 54, in alternative embodiments, the control 40 can be a part of the gantry 12 or the processor 54. The processor 54 is configured to send prompting signals to the patient prompting device 100 in a prescribed manner (e.g., in synchronization with a rotation of the gantry 12).

The patient prompting device 100 is configured to provide visual signals to the patient 16 during a procedure, thereby instructing the patient 16 to perform certain task(s). The patient prompting device 100 includes a screen 101, an image source 104, and a structure 106 to which the screen 101 and the image source 104 are coupled. The structure 106 has a low profile, thereby allowing the screen 101 be placed within the opening 13 of the gantry. The screen 101 is preferably made from a non-metallic material and does not include circuitry for preventing interference with a radiation field. In the illustrated embodiments, the screen 101 has a mirror surface, and the image source 104 includes a flat panel screen (or a monitor screen). During use, the image source 104 receives image data from the processor 54 and displays graphics in response thereto. The graphics is reflected by the mirror surface, and the patient 16 can see the reflected graphics by looking towards the mirror surface 102. In other embodiments, the screen 101 can include a non-mirror (e.g., a non-reflective) surface. In such cases, instead of the image source 104 being a flat panel or a screen, the image source 104 includes an image projector that projects image onto the surface. Also, in other embodiments, the image source 104 can include fiber optics for transmitting image signals to a viewing surface. In such case, the screen 101 can be a component of a glasses or goggles, with the viewing surface being an inside face of the glasses or goggles. Other types of image source can also be used in alternative embodiments. For example, in further embodiments, the screen 101 can itself be a LCD screen (an image source) provided that its electronics do not significantly interfere with a radiation field. In such cases, the patient prompting device 100 does not include the image source 104. The above described embodiments of the patient prompting device 100 has been described in U.S. Patent Application entitled, "Patient Multimedia Display", filed concurrently with this application. Other display mechanism can also be used as long as it provides a viewing surface from which the patient 16 can receive image signals. In the illustrated embodiments, the image/graphics as shown in the screen 101 provides visual signal to control the patient's breathing (e.g., by instructing the patient 16 to hold breath, to inhale, and/or to exhale) while the gantry 12 rotates around the patient 16 to collect image data, thereby ensuring that CT image data that correspond to a prescribed phase of a breathing cycle are obtained. However, in other embodiments, the image/graphics as shown in the screen 101 can be configured to instruct the patient 16 to perform other task(s).

The system 10 also includes a position monitoring system 200 for monitoring a position of a portion of the patient 16, and producing a position signal in response thereto. The position signal is transmitted to the processor 54, which causes the image source 104 to generate a visual indicator representing a position of the patient portion. In the illustrated embodiments, the position monitoring system 200 includes a marker block 202 placed on the patient 16, and an optical device 204 coupled to the processor 54. The optical device 204 may be a camera or other imaging devices, and is configured to sense an image of the marker block 202. The marker block 202 preferably comprises a reflective or retro-reflective material that can reflect light, whether in the visible or invisible wavelengths. The marker block 202 has a rectangular shape with multiple retro-reflective elements 203 located on its surface. Alternatively, the marker block 202 can have a different shape, such as a hemispherical shape, or a disk shape, as long as the size, spacing, and position of the reference locations are configured such that the optical device 204 can view and generate an image that accurately shows the positioning of the marker block 202.

When using the position monitoring system 200, one or more marker block 202 is placed on or secured to the patient 16, and the optical device 204 is used to sense the marker block(s) 202. The optical device 204 produces a set of image coordinates for the marker elements on the marker block(s) 202. The position and distance of the marker elements located on the marker block(s) 202 is known relative to other marker elements on the same respective marker block(s) 202. By comparing the position and distance between the marker elements on a recorded image frame with a reference position and image stored for the position monitoring system 200, the absolute position and orientation of the marker block(s) 202 can be determined with a high degree of accuracy. This, in turn, provides an accurate position and orientation estimation for the patient position or the patient body position upon which the marker block(s) 202 is attached. Such and similar physiological gating systems have been described in U.S. Pat. No. 6,621,889, and U.S. patent application Ser. No. 09/893, 122, filed Jun. 26, 2001, the entire disclosures of which are expressly incorporated by reference herein.

It should be noted that other types of patient position monitoring system can also be used. For example, in alternative embodiments, instead of using an optical system, another device, such as a spirometer, strain-gauge, a laser sensor, a pressure sensor, or any of other devices known in the art of position or activity state monitoring, can be used to sense and/or measure a patient movement or an activity state during a procedure.

Patient Prompting Interface

During a CT image acquisition procedure, as the radiation source 20 is rotated about the patient 16 to generate CT image data at a plurality of gantry rotational angles, the patient prompting system 100 is used to guide the patient 16 to control his/her breathing such that one or more breathing state of the patient 16 can be synchronized with the rotation of the gantry 12, thereby allowing desired image quality to be obtained at prescribed gantry angles. Particularly, the processor 54 is configured (e.g., programmed) to cause the image source 104 to provide visual signals for prompting the patient 16 during a procedure based on signals/data received from the optical device 204 and a rotational position of the gantry 12 (or the radiation source 20).

Figure 2A:
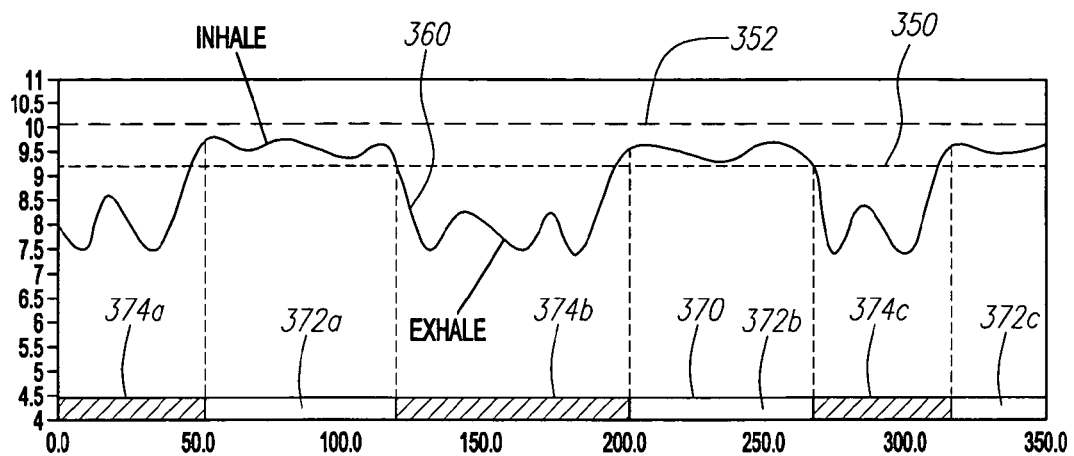
FIG. 2A-2C illustrates examples of breathing waveforms relative to gantry rotational angles.
Figure 2B:
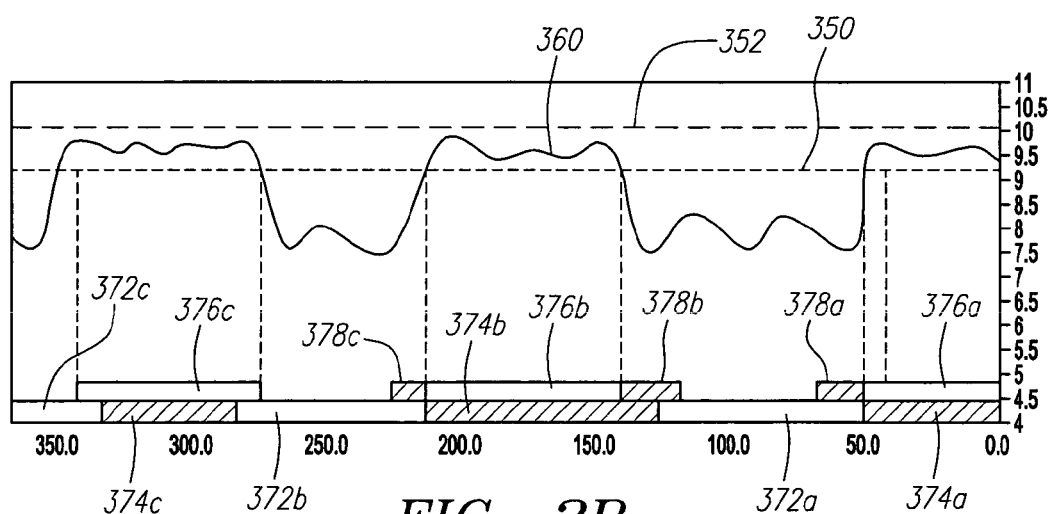
Figure 2C:
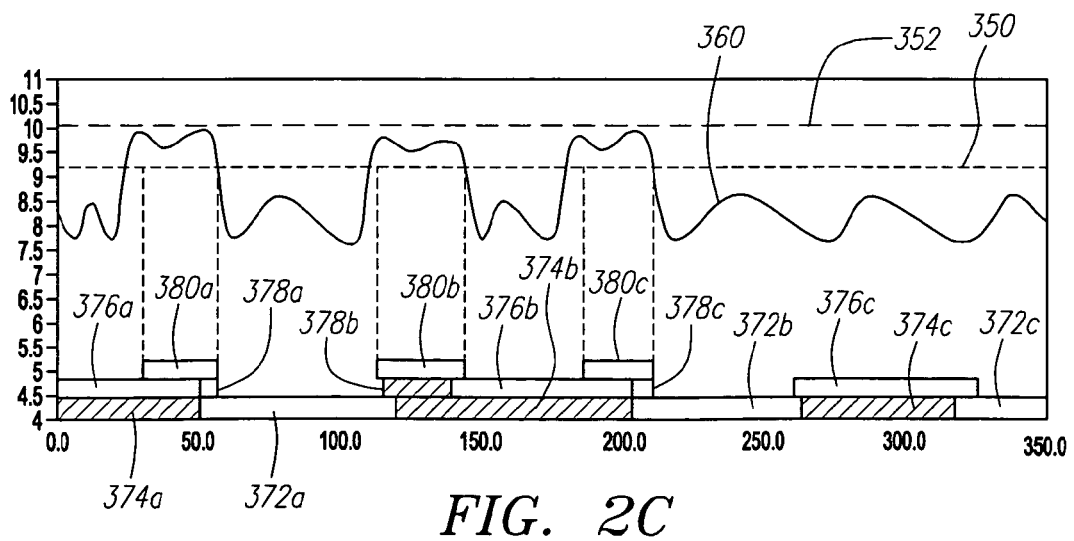

FIGS. 2A-2C illustrate examples of the patient's breathing waveforms as the gantry 12 rotates around the patient's 16 to collect image data. As the gantry 12 rotates 360° around the patient 16 in a first direction during a first rotation, the patient 16 undergoes a plurality of breathing cycles (the amplitude of which is represented by curve 360). When the patient's inhale level satisfies a prescribed criteria (e.g., lies between a minimum prescribed inhale level and a maximum prescribed inhale level, represented by lines 350, 352, respectively), the processor 54 then causes the radiation source 20 to activate to deliver a radiation beam and generate CT image data. Similarly, when the patient's inhale level falls outside the boundaries 350, 352, the processor 54 then causes the radiation source 20 to deactivate and cease generating CT image data. Alternatively, the radiation source 20 can continue to transmit radiation at a plurality of gantry rotational angles even when the patient's inhale level falls outside the prescribed range. In such cases, the processor 54 maintains a record of the CT image data that are collected, and chooses only desired CT image data (e.g., CT image data that correspond to a desired breathing level) for reconstruction of tomography image(s).

As shown in FIG. 2A, during a first gantry rotation, CT image data are collected at gantry angles that are between 50°-120°, 210°-275°, and 325-360° (represented by clear portions 372a, 372b, 372c, respectively, of a bar 370), with CT image data desired to be collected at remaining gantry angles represented by hatched portions 374a, 374b, 374c of the bar 370.

During a next gantry rotation, the gantry 12 rotates (e.g., in an opposite direction), and additional CT image data are collected at gantry angles that correspond to the patient's inhale level satisfying the prescribed criteria (e.g., inhale level lying between prescribed levels 350, 352). As shown in FIG. 2B, during the second gantry rotation, with the aid of the patient prompting device 100, the patient 16 attempts to cause additional CT image data be collected by trying to match his/her breathing with the portions 374a-374c. As a result, additional CT image data are collected at gantry angles at which image data (or desirable image data) were not previously obtained in the first gantry rotation. In the illustrated example, CT image data are collected at gantry angles that are between 0°-50°, 140°-210°, and 260°-330°, corresponding to portions 376a, 376b, 376c shown in the graph, with CT image data desired to be collected at remaining gantry angles that are represented by hatched portions 378a, 378b, 378c.

In some embodiments, it may be desirable to have CT image data collected from one gantry rotation overlap CT image data collected from another gantry rotation. For example, although image data have been collected between gantry rotational angles 210°-275° (corresponding to portion 372b) during the first gantry rotation, and image data have been collected between gantry rotational angles 140°-210° (corresponding to portion 376b) during the second gantry rotation, it may be desirable to have additional image data collected at or adjacent the seam between the two portions 372b, 376b. As such, in the illustrated example, hatched portion 378a is shown to correspond to a portion of a gantry rotation at which overlapping image data are desired. Similar is true for portion 378a and part of portion 378b. In alternative embodiments, CT image data collected from one gantry rotation is not required to overlap CT image data collected from another gantry rotation.

During a next gantry rotation, the gantry 12 rotates (e.g., in an opposite direction from that of the last rotation), and additional CT image data are collected at gantry angles that correspond to the patient's inhale level satisfying the prescribed criteria. As shown in FIG. 2C, during the third gantry rotation, with the aid of the patient prompting device 100, the patient 16 attempts to cause additional CT image data be collected by trying to match his/her breathing with the portions 378a-378c. As a result, additional CT image data are collected at gantry angles at which image data (or desirable image data) were not obtained in the first and the second gantry rotations. In the illustrated example, CT image data are collected at portions 380a, 380b, 380c of the gantry rotation. When all desired image data have been collected, the CT image data acquisition procedure is then terminated. Although the CT image data acquisition procedure has been described with reference to the gantry 12 making three gantry rotations in the illustrated example, it should be understood that a CT image data acquisition procedure may require more or less than three gantry rotations.

Figure 3A:
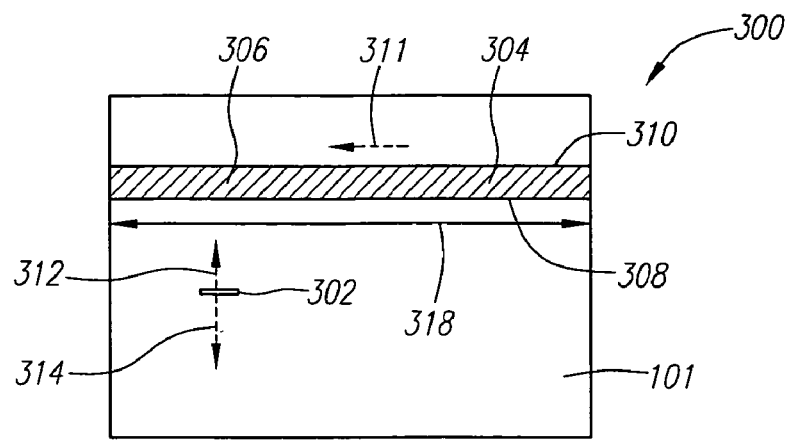
FIG. 3A-3C illustrate a user interface in accordance with some embodiments of the invention.
Figure 3B:
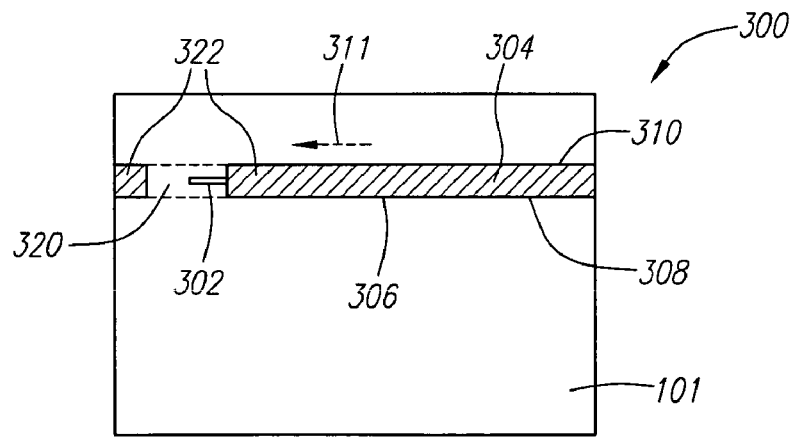
Figure 3C:
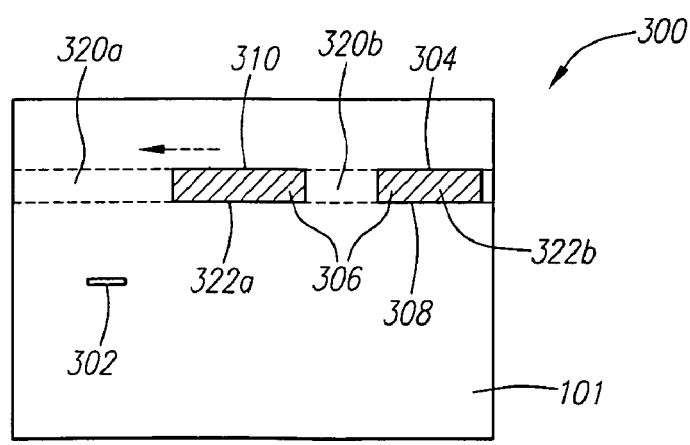

As mentioned previously, the patient prompting device 100 assists or guides the patient 16 in controlling his/her breathing during a CT image data acquisition procedure. FIG. 3A-3C illustrate a user interface 300 for prompting the patient 16 in accordance with some embodiments of the invention. The user interface 300 includes a first indicator (displayed object) 302 for indicating a state/result of a patient activity, and a second indicator (displayed object) 304 for indicating a target state/target result of the patient activity. The first and the second indicators 302, 304 are displayed in the screen 101 of the patient prompting device 100. The first indicator 302 includes a bar, the position of which relative to the screen 101 represents a breathing level of the patient 16. In the illustrated embodiments, the optical device 204 generates an image of the marker block 202, and transmits image signals to the processor 54. The processor 54 analyzes the image signals to determine the position and/or orientation of the marker block 202, and output a signal to cause the image source 104 to display the first indicator 302 at a position in the screen 101 that is indicative of, or associated with, the determined position and/or orientation of the marker block 202. As such, as the patient 16 breaths, the marker block 202 moves in response to the patient's breathing, and the processor 54 in turn causes the first indicator 302 to move in correspondence with the patient's breathing. In the illustrated embodiments, when the patient 16 inhales, the first indicator 302 moves in a first direction 312, and when the patient 16 exhales, the first indicator 302 moves in a second direction 314.

As shown in FIG. 3A, the second indicator 304 includes a bar 306 having a first line 308, and a second line 310. The first line 308 represents a prescribed minimum inhale level of a breathing, and the second line 310 represents a prescribed maximum inhale level of a breathing. The bar 306 also has a length 318, which represents at least a portion of a range of gantry angles at which CT image data is desired to be collected. In some embodiments, the length of the bar 306 represents an entire range of gantry angles at which CT image data are desired to be collected. Alternatively, the bar 306 as displayed in the screen 101 represents different portion(s) of an entire range of gantry angles at which CT image data are desired to be collected as the bar 306 moves across the screen 101. During use, the processor 54 receives an instantaneous gantry angle read-out, and generate the bar 306 (or at least portion(s) thereof) based on the instantaneous gantry angle. The bar 306 moves in a direction indicated by arrow 311, and in synchronization with a rotation of the gantry 12 (or the radiation source 20). The patient 16 is instructed (either before or during a radiation procedure) to move the first indicator 302 in between the first and the second lines 308, 310 by inhaling, and keep the first indicator 302 in between the first and the second lines 308, 310 by breath-holding.

When the first indicator 302 has been positioned by the patient 16 in between the first and the second lines 308, 310, the processor 54 sends a "ON" signal to activate the radiation source 20, thereby creating CT image data. The radiation source 20 is activated at a plurality of gantry rotational angles as the gantry 12 is rotated about the patient 16 as long as the first indicator 302 is between the first and the second lines 308, 310 (representing a desired breathing state for collecting CT image data). When the patient 16 no longer holds his/her breath within the prescribed range inhale levels, the patient 16 will exhale, causing the first indicator 302 to move out of the prescribed range of inhale levels. In such cases, the processor 54 sends a "OFF" signal to deactivate the radiation source 20 to cease transmitting radiation. Such feature is advantageous because it minimizes an amount of radiation delivered to the patient 16. However, in alternative embodiments, the radiation source 20 can continue to transmit radiation at a plurality of gantry rotational angles even when the first indicator 302 has moved out of the prescribed range of inhale levels. In such cases, the processor 54 maintains a record of the CT image data that are collected, and chooses only the desired image data (e.g., image data that correspond to desired breathing level) for reconstruction of tomography image(s).

As FIG. 3B shows, after the patient 16 has moved the first indicator 302 in between the first and the second lines 308, 310, a portion 320 of the bar 306 where the first indicator 302 intercepts the bar 306 changes color (or appears to be removed if the changed color is similar to a background color). The portion 320 represents part of the prescribed range of gantry angles at which CT image data has been collected, while a remaining portion(s) 322 of the bar 306 represents the part(s) of the prescribed range of gantry angles at which CT image data are still desired to be collected. Since the bar 306 is moving in the direction 311 in synchronization with the gantry 12 rotation, more portion of the bar 306 will change color (or the portion 320 will grow) as long as the patient 16 controls his/her breathing to maintain the first indicator 302 between the first and the second lines 308, 310.

When the patient 16 exhales, the first indicator 302 moves out of the location between the first and the second lines 308, 310 in response thereto, and the bar 306 ceases changing. However, the bar 306 continues to move in the direction 311 in correspondence with a rotation of the gantry 12. The patient 16 can repeat the step of inhaling to move the first indicator 302 between the first and the second lines 308, 310 again to cause another portion of the bar 306 to change color (or to be removed)—thereby causing CT image data to be collected at additional gantry rotational angles. For example, during a CT image acquisition procedure, the patient 16 can inhale and exhale for a plurality of times, resulting in a plurality of portions 320a, 320b of the bar 306 changing color (or being removed), with the remaining portions 322a, 322b of the bar 306 representing the parts of the prescribed range of gantry angles at which CT image data are still desired to be collected (FIG. 3C). In some embodiments, the processor 54 is configured to make adjustment to the bar 306 such that additional (or overlapping) CT image data can be collected (e.g., at a range of gantry angles that are adjacent to that represented by the interface between the portion 322a and the portion 320b). For example, the processor 54 can be configured to change at least a part of a removed portion 320 back to a hatched portion 322.

In the illustrated embodiments, the uncovered gantry angle intervals resulting from the patient's breathing being non-compliance defines the configuration of the bar 306 (e.g., spacing and length of the remaining portions (or indicator boxes) 322) for the next gantry rotation. As remaining portion (s) of the bar 306 approach the first indicator 302 a second time (corresponding to a second gantry rotation), the patient 16 can repeat the breathing step(s) in an attempt to cause additional CT image data be collected at remaining gantry angles at which CT image data were not previously collected. The gantry 12 continues to make additional rotation, and the user interface 300 continues to display remaining portions of the bar 306 (e.g., based on an instantaneous gantry angle read-out), until the patient 16 has caused the entire bar 306 to change color (or the entire bar 306 to be removed), representing the condition that CT image data at all prescribed gantry rotational angles have been collected.

Providing the first indicator 302 is advantageous because it informs the patient 16 a relationship between a result of an activity being performed by the patient, and a first target result desired to be achieved by the activity, thereby allowing the patient 16 to gauge himself/herself while performing the activity. For example, the patient 16 can breath harder or less based on a position of the first indicator 302 as observed by the patient 16. In addition, providing the second indicator 304 is also advantageous because it informs the patient 16 a relationship between a time and a target result desired to be achieved by an activity, thereby allowing the patient 16 to decide when to perform a certain task based on his/her own awareness of a target result desired to be accomplished. The combination of these two features allows a patient to control his/her breathing such that CT image data at prescribed range (s) of gantry angles can be collected efficiently.

Figure 4:
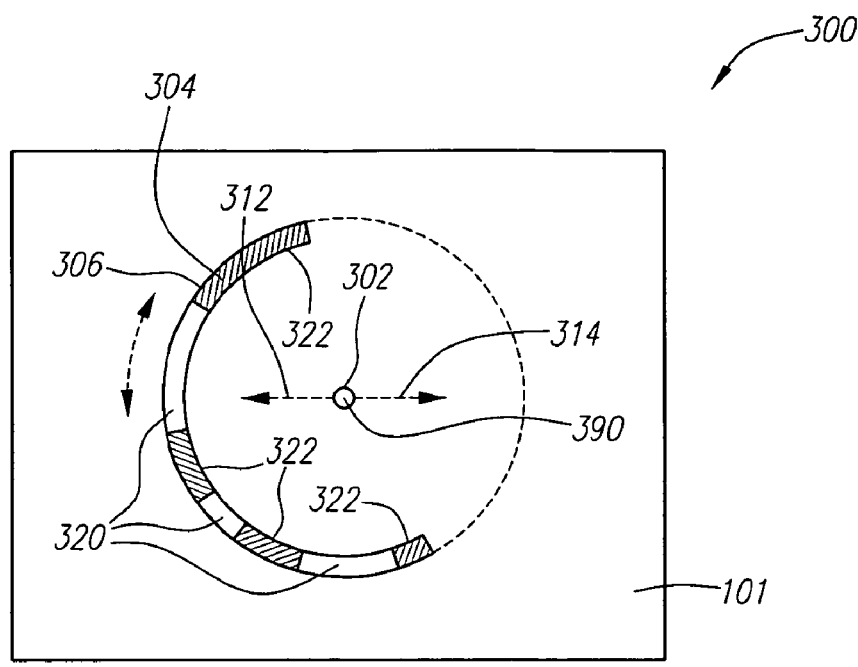
FIG. 4 illustrates a user interface having a curvilinear bar in accordance with other embodiments of the invention.

It should be noted that the user interface 300 should not be limited by the example described previously, and that the user interface 300 can have other configurations in alternative embodiments. FIG. 4 illustrates a variation of the user interface 300. In such cases, instead of having a straight profile, the bar 306 has a profile that resembles a portion of a circle. The arc angle of the bar 306 corresponds to a prescribed range of gantry angles at which CT image data are desired to be collected. During use, the bar (in the form of an arc) rotates about a center 390 in a direction and speed that corresponds to a rotation of the gantry 12 (or the radiation source 20), and the patient 16 is instructed (either before or during a radiation procedure) to move the first indicator 302 in the first direction 312 (e.g., by inhaling) such that the first indicator 302 intercepts the bar 306, as similarly described previously. Initially, the bar 306 has a first color (represented by hatch in the example). As the patient 16 successfully causes the first indicator 302 to intercept the bar 306, portion(s) 320 of the bar 306 changes color (or is removed), indicating to the patient 16 that the CT image data at the corresponding gantry angles have been collected. The patient 16 continues to control his/her breathing to cause the first indicator 302 to intercept remaining portion(s) 322 as the bar 306 rotates about the center 390 (either continuously in one direction, or in a back-and-forth manner), until CT image data at all prescribed gantry angles have been collected. In alternative embodiments, instead of the bar 306 being an arc, the bar 306 can be a complete circle.

In the above embodiments, the user interface 300 is configured to guide the patient's breathing by prescribing a range of inhale levels. In alternative embodiments, the user interface 300 can be configured to guide the patient's breathing by prescribing a range of exhale levels. In such cases, the user interface 300 includes lines that represent a minimum exhale level and a maximum exhale level (that are similar to the minimum and maximum inhale levels 308, 310 discussed previously).

Figure 5:
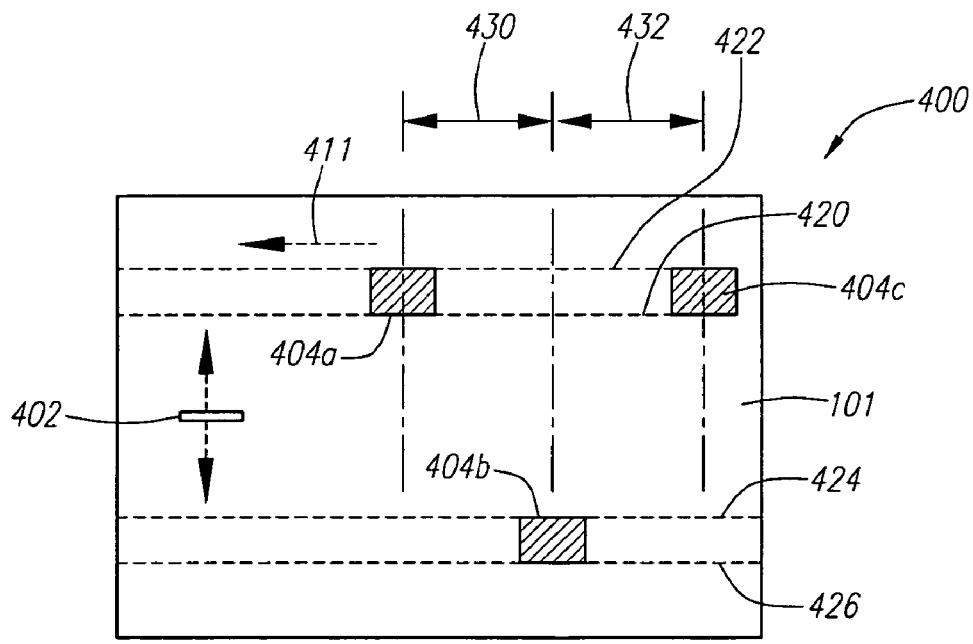
FIG. 5 illustrates a user interface in accordance with other embodiments of the invention, showing the interface displaying graphics that represent prescribed inhale and exhale levels of a breathing.

In further embodiments, the user interface 300 can be configured to guide a patient's breathing by prescribing both ranges of inhale and exhale levels. FIG. 5 illustrates a user interface 400 for prompting a patient in accordance with other embodiments of the invention. The user interface 400 includes a first indicator (displayed object) 402 for indicating a state/result of a patient activity, and a plurality of indicators (displayed object) 404 representing target state/target result of the patient activity. The indicators 402, 404 are displayed in the screen 101 of the patient prompting device 100. The first indicator 402 includes a bar, the position of which relative to the screen 101 represents a breathing level of the patient 16. In the illustrated embodiments, the optical device 204 generates an image of the marker block 202, and transmits image signals to the processor 54. The processor 54 analyzes the image signals to determine the position and/or orientation of the marker block 202, and output a signal to cause the image source 104 to display the first indicator 302 at a position in the screen 101 that is indicative of, or associated with, the determined position and/or orientation of the marker block 202. As such, as the patient 16 breaths, the marker block 202 moves in response to the patient's breathing, and the processor 54 in turn causes the first indicator 302 to move in correspondence with the patient's breathing.

As shown in FIG. 5, the first target 404a represents a prescribed inhale level desired to be accomplished by the patient 16. The target 404a has bottom and top sides that correspond to a minimum inhale level 420 and a maximum inhale level 422, respectively. Similar is true for the target 404c. The second target 404b represents a prescribed exhale level desired to be accomplished by the patient 16. The target 404*b* has top and bottom sides that correspond to a minimum exhale level 424 and a maximum exhale level 426, respectively. In some embodiments, the distances (e.g., distances, 430, 432) between successive targets 404 can be adjusted, depending on a particular need of a procedure. Also, in other embodiments, a length of a target can be adjusted, e.g., made longer to indicate that a breath-hold is desired. In some embodiments, the prescribed inhale level, the prescribed exhale level, and the distances 430, 432 are user specific, and can be determined during a training session. Such will make the patient more comfortable because the interface is prescribing a manner of breathing in which the patient is accustomed to performing.

During use of the interface 400, the targets 404 move in a direction indicated by arrow 411, and in synchronization with a rotation of the gantry 12 (or the radiation source 20). The patient 16 is instructed (either before or during a radiation procedure) to move the first indicator 402 to intercept the targets 404, e.g., one after the other, by inhaling and exhaling, as the targets 404 moves across the screen 101, thereby controlling substantially all phases of the patient's breathing cycle. Such result is particularly desirable in the case in which sets of image data are desired to be collected for different prescribed phases of a breathing cycle, which requires patient breathing period to be as constant as possible and the phase of the periodic breathing motion to be synchronized with the gantry angle at any given time. In the illustrated embodiments, the processor 54 is configured to activate the radiation source 20 to generate image data when the first indicator 402 intercepts a target (one of the targets 404), and deactivate the radiation source 20 when the first indicator 402 misses a target. In some embodiments, a physician can prescribe a number N of phases into which a breathing cycle is divided. In such cases, the processor 54 is configured to provide appropriate visual signals via the patient prompting interface 400, and to provide timing signals to the gantry control 40 such that sets of image data for each of the N prescribed phases of a breathing cycle can be collected.

In other embodiments, instead of collecting CT image data for each of the N phases of a breathing cycle, CT image data are collected only for a desired phase range of a breathing cycle. For example, a breathing cycle may be divided into N=3 intervals, but CT image data may be desired to be collected for only the first ⅓ of a breathing cycle. In such cases, the patient prompting interface 400 can accordingly be configured to provide appropriate visual signals to the patient 16 such that the patient 16 can control his/her breathing at the right time to enable all desired CT image data be collected for the first ⅓ of the breathing cycle. Moreover, in some cases, fewer rotations can be used by foregoing having data for the entire 360° coverage for the phase(s) of interest and instead having data for such phase(s) from a sufficient number of angles to produce an image of sufficient quality for the purpose at hand.

If CT image data for all prescribed phases of a breathing cycle have been collected, then the CT image data collection process is terminated, and CT images are reconstructed using the collected CT image data. The reconstruction of CT images may be performed using a technique or method known in the art. In one embodiment, the processor 54 sorts the CT image data according to the phase segment of the respiratory cycle at which it was acquired, and synchronizes the collected CT image data such that data corresponding to a given phase of a respiratory cycle are combined to reconstruct an image for that phase. When CT images for all phases of a respiratory cycle have been reconstructed, the CT images may be displayed in a sequence to form a video.

Figure 6:
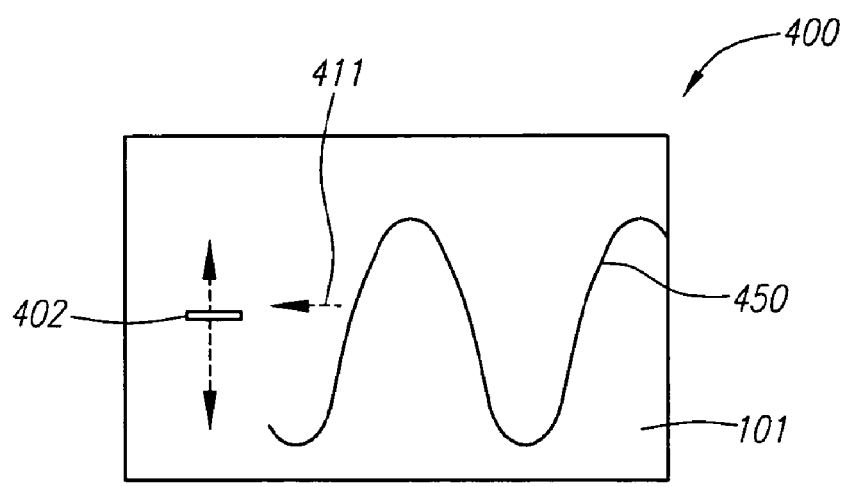
FIG. 6 illustrates a user interface in accordance with other embodiments of the invention, showing the interface displaying a curve that represents a target breathing motion.

It should be noted that the configuration of the user interface 400 is not limited by the examples discussed previously, and that the user interface 400 can have other configurations in alternative embodiments. For example, instead of targets 404 that are in the form of a block, in alternative embodiments, the user interface 400 can display a curve 450 that represents desired breathing waveforms to be accomplished (FIG. 6). In such cases, the curve 450 is configured to move across the screen 101 in the direction 411, and the patient 16 is instructed (either before or during a radiation procedure) to move the first indicator 402, e.g., by inhaling and exhaling, such that the first indicator 402 stays on the curve 450 as much as possible, as the curve 450 moves across the screen 101. In the illustrated example, the curve 450 has a shape that resembles a sine wave, but can have other shapes, such as a customized shape, in other embodiments. For example, the shape of the curve 450 can be specific to each patient and can be obtained in a training session. In the illustrated embodiments, the processor 54 sends a "ON" signal to activate the radiation source 20 to emit radiation for generating CT image data when the first indicator 402 intercepts the curve 450, and a "OFF" signal to deactivate the radiation source 20 when the first indicator 402 does not intercept the curve 450. In some embodiments, after image data at a desired gantry rotational angle have been collected for a prescribed phase of a breathing cycle, the processor 504 can change a color of (or remove) the corresponding portion of the curve 450 to indicate that image data have been collected for the corresponding gantry angle. The user interface 400 continues to display the curve 450 across the screen 101, and the patient 16 continues to operate the first indicator 402 by breathing, until CT image data for all prescribed gantry rotational angles and for all prescribed phases of a breathing cycle are collected.

Figure 7:
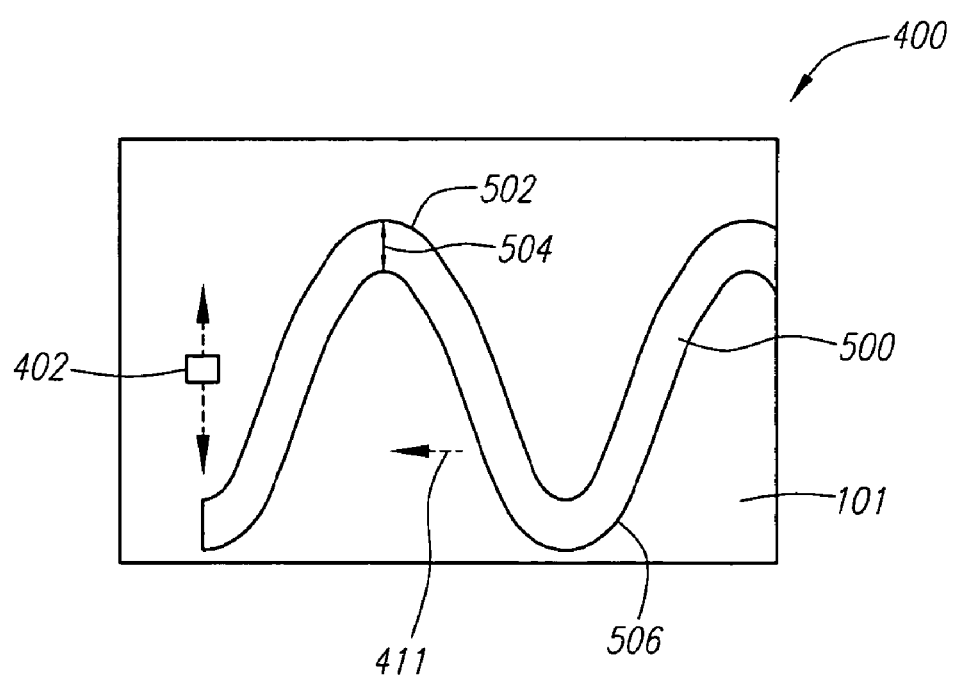
FIG. 7 illustrates a user interface in accordance with other embodiments of the invention.

FIG. 7 shows a variation of the user interface 400, which includes a curve 500 having a first side 502 and a second side 506. In such cases, the curve 500 is configured to move across the screen 101 in the direction 411, and the patient 16 is instructed (either before or during a radiation procedure) to move the first indicator 402, e.g., by inhaling and exhaling, such that the first indicator 402 stays in between the first and the second sides 502, 506 as the curve 500 moves across the screen 101. The sides/boundaries 502, 506 are separated by a distance 504, which represents a range of prescribed breathing levels at which image data will be collected. The distance 504 can be uniform along a length of the curve 500, or alternatively, can vary along a length of the curve 500. In the illustrated example, the curve 500 has a shape that resembles a sine wave, but can have other shapes, such as a customized shape, in other embodiments. In the illustrated embodiments, the processor 54 sends a "ON" signal to activate the radiation source 20 to emit radiation for generating CT image data when the first indicator 402 is within the boundaries 502, 506 of the curve 500, and a "OFF" signal to deactivate the radiation source 20 when the first indicator 402 is outside the boundaries 502, 506. In some embodiments, after CT image data at a desired gantry rotational angle have been collected for a prescribed phase of a breathing cycle, the processor 504 can change a color of (or remove) the corresponding portion of the curve 500 to indicate that image data have been collected. The user interface 400 continues to display the curve 500 across the screen 101, and the patient 16 continues to operate the first indicator 402 by breathing, until CT image data for all prescribed gantry rotational angles and for all prescribed phases of a breathing cycle are collected.

Although several examples of a patient prompting interface have been described, it should be noted that the scope of the invention should not be so limited. In alternative embodiments, the user interfaces 300, 400 can have other configurations for informing a patient a relationship between a result of an activity being performed by the patient, and a first target result desired to be achieved by the activity and/or a relationship between a time and the target result desired to be achieved by an activity. For example, in alternative embodiments, instead of a bar (e.g., the bar 306), the processor 54 can be configured to display an object having a different form for prompting the patient 16. As used in this specification, the term "object" can include any item, such as a graph, a text, a number, a message, a symbol, a line, a bar, an object having a geometric or customized shape, etc. In other embodiments, instead of the object being displayed, an "object" can be one or more lights emitted by an optical device. Also, instead of each indicator being an object, in other embodiments, two or more indicators can be represented by a single object, or alternatively, an indicator can be represented by two or more objects. In addition, in other embodiments, the processor 54 can be configured to cause CT image data be collected when a patient's inhale (or exhale) level has reached a minimum prescribed level, regardless of how much the patient's inhale (or exhale) level exceed the minimum prescribed level. In such cases, the user interface does not have an indicator for representing a maximum inhale (or exhale) level.

In further embodiments, the patient prompting device 100 can further include a speaker. In such cases, the processor 54 can be configured to cause the speaker to emit audio signal(s) for prompting the patient 16. Also, in any of the embodiments described herein, the processor 54 can be configured to provide a visual signal or an audio signal when a desired task has been performed by the patient 16. For example, the visual signal can be a score, and the audio signal can be a game sound, thereby providing a game interface for prompting the patient 16, which may make the image acquisition procedure more fun and engaging for the patient 16.

Computer System Architecture

FIG. 8 is a block diagram that illustrates an embodiment of a computer system 800 upon which an embodiment of the invention may be implemented. Computer system 800 includes a bus 802 or other communication mechanism for communicating information, and a processor 804 coupled with the bus 802 for processing information. The processor 804 may be an example of the processor 54, or alternatively, an example of a component of the processor 54, of FIG. 1. The computer system 800 also includes a main memory 806, such as a random access memory (RAM) or other dynamic storage device, coupled to the bus 802 for storing information and instructions to be executed by the processor 804. The main memory 806 also may be used for storing temporary variables or other intermediate information during execution of instructions to be executed by the processor 804. The computer system 800 further includes a read only memory (ROM) 808 or other static storage device coupled to the bus 802 for storing static information and instructions for the processor 804. A data storage device 810, such as a magnetic disk or optical disk, is provided and coupled to the bus 802 for storing information and instructions.

The computer system 800 may be coupled via the bus 802 to a display 87, such as a cathode ray tube (CRT), for displaying information to a user. An input device 814, including alphanumeric and other keys, is coupled to the bus 802 for communicating information and command selections to processor 804. Another type of user input device is cursor control 816, such as a mouse, a trackball, or cursor direction keys for communicating direction information and command selections to processor 804 and for controlling cursor movement on display 87. This input device typically has two degrees of freedom in two axes, a first axis (e.g., x) and a second axis (e.g., y), that allows the device to specify positions in a plane.

Embodiments of the invention are related to the use of computer system 800 for generating visual signals for prompting a patient. According to one embodiment of the invention, such use is provided by computer system 800 in response to processor 804 executing one or more sequences of one or more instructions contained in the main memory 806. Such instructions may be read into the main memory 806 from another computer-readable medium, such as storage device 810. Execution of the sequences of instructions contained in the main memory 806 causes the processor 804 to perform the process steps described herein. One or more processors in a multi-processing arrangement may also be employed to execute the sequences of instructions contained in the main memory 806. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to the processor 804 for execution. Such a medium may take many forms, including but not limited to, non-volatile media, volatile media, and transmission media. Non-volatile media includes, for example, optical or magnetic disks, such as the storage device 810. Volatile media includes dynamic memory, such as the main memory 806. Transmission media includes coaxial cables, copper wire and fiber optics, including the wires that comprise the bus 802. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 804 for execution. For example, the instructions may initially be carried on a magnetic disk of a remote computer. The remote computer can load the instructions into its dynamic memory and send the instructions over a telephone line using a modem. A modem local to the computer system 800 can receive the data on the telephone line and use an infrared transmitter to convert the data to an infrared signal. An infrared detector coupled to the bus 802 can receive the data carried in the infrared signal and place the data on the bus 802. The bus 802 carries the data to the main memory 806, from which the processor 804 retrieves and executes the instructions. The instructions received by the main memory 806 may optionally be stored on the storage device 810 either before or after execution by the processor 804.

The computer system 800 also includes a communication interface 818 coupled to the bus 802. The communication interface 818 provides a two-way data communication coupling to a network link 820 that is connected to a local network 822. For example, the communication interface 818 may be an integrated services digital network (ISDN) card or a modem to provide a data communication connection to a corresponding type of telephone line. As another example, the communication interface 818 may be a local area network (LAN) card to provide a data communication connection to a compatible LAN. Wireless links may also be implemented. In any such implementation, the communication interface 818 sends and receives electrical, electromagnetic or optical signals that carry data streams representing various types of information.

The network link 820 typically provides data communication through one or more networks to other devices. For example, the network link 820 may provide a connection through local network 822 to a host computer 824 or to medical equipment 826 such as a radiation beam source or a switch operatively coupled to a radiation beam source. The data streams transported over the network link 820 can comprise electrical, electromagnetic or optical signals. The signals through the various networks and the signals on the network link 820 and through the communication interface 818, which carry data to and from the computer system 800, are exemplary forms of carrier waves transporting the information. The computer system 800 can send messages and receive data, including program code, through the network (s), the network link 820, and the communication interface 818.

Although the embodiments of the systems and methods have been described with reference to generating CT images while passively controlling a patient's breathing in a synchronized manner, it should be understood that the systems and methods may also be implemented to control other physiological motions in different medical (which may or may not involve a radiation source) or non-medical procedures. In addition, although the gantry 12 has been described as making a 360° rotation around the patient 16 during CT image data acquisition, such needs not be the case. For example, if a full cone detector is used, the system 10 may acquire data while the gantry 12 rotates 180° plus the angle of the beam pattern. Other angles of rotation may also be used, depending on the particular system being employed and the particular need of an application. For example, in some procedures, it may be desirable to obtain image data (which may, for example, be incomplete for the purpose of performing 3D reconstruction) at certain prescribed of gantry angle(s). In such cases, the processor 54 can be configured to generate visual signals (that correspond to the prescribed range(s) of gantry angles) on the screen 101 for prompting the patient 16 accordingly. Also, instead of rotating the gantry 12 in alternating opposite directions in successive rotations, in alternative embodiments, the gantry 12 can be configured to rotate in a same direction in successive rotations. Furthermore, instead of a CT procedure, the above described user interfaces or similar user interfaces can be implemented in a laminar tomography procedure, a MRI procedure, a PET procedure, or other imaging procedures, in which a plurality of image data is desired to be generated. As such, the gantry 12 should not be limited to a rotatable structure as described previously, and could have other configurations, such as a sliding or translating configuration, depending on the particular application or procedure.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. For example, the operations performed by the processor 54 can be performed by any combination of hardware and software within the scope of the invention, and should not be limited to particular embodiments comprising a particular definition of "processor". Also, the term "image" as used in this specification includes image data that may be stored in a circuitry or a computer-readable medium, and should not be limited to image data that is displayed visually. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A method of prompting a patient during a medical procedure, comprising:
displaying a first graphic on a screen for viewing by the patient, wherein the first graphic is generated using a processor, wherein the first graphic comprises a first row of one or more objects and a second row of one or more objects, and wherein one of the one or more objects in the first row represents a first target result that is desired to be accomplished by a breathing motion of the patient;
displaying a second graphic on the screen, wherein the second graphic represents a breathing state of the patient;
moving the first graphic in accordance with a predetermined medical plan; and
moving the second graphic in response to the breathing motion of the patient;
wherein the first row comprises a first horizontal row, the second row comprises a second horizontal row, and the act of moving the first graphic comprises moving the one or more objects in the first row and the one or more objects in the second row horizontally.

2. The method of claim 1, wherein the first target result comprises a prescribed inhale level of a breathing, a prescribed exhale level of a breathing, or a prescribed duration of a breath-hold.

3. The method of claim 1, wherein the one of the one or more objects in the first row is associated with a portion of a gantry rotation, and has a length that represents a prescribed duration of a breath-hold.

4. The method of claim 1, wherein the act of moving the first graphic is performed in synchronization with a movement of a medical device.

5. The method of claim 4, wherein the medical device comprises a radiation source.

6. The method of claim 1, wherein the displayed first and second graphics are configured to allow the patient to decide when to begin the breathing motion in order to accomplish the first target result by a future time.

7. The method of claim 1, wherein the first graphic has a feature representing a range of positions of a radiation source at which radiation will be provided by the radiation source.

8. The method of claim 1, wherein the first target result is desired to be accomplished by a future time, and the first graphic is configured for indicating to the patient when the future time will arrive.

9. The method of claim 1, wherein the first and the second graphics are configured to provide an indication to the patient of a relationship among the breathing state of the patient, a desired breathing level to be accomplished, and a future time by which to accomplish the desired breathing level.

10. The method of claim 1, wherein a position of the one of the one or more objects in the first row relative to a reference point indicates a remaining duration before a future time for accomplishing the first target result will arrive.

11. The method of claim 1, wherein the medical procedure comprises an imaging procedure.

12. The method of claim 1, further comprising changing a configuration of at least a part of the first graphic in response to the patient accomplishing at least part of the first target result.

13. The method of claim 1, wherein another one of the one or more objects in the first row represents a second target result that is desired to be accomplished.

14. The method of claim 1, wherein the one or more objects in the first row and the one or more objects in the second row are arranged in a staggered configuration.

15. The method of claim 1, wherein each of the one or more objects in the first row comprises a rectangular block.

16. A method of prompting a patient during a medical procedure, comprising:
   displaying a first graphic on a screen for viewing by the patient, wherein the first graphic is generated using a processor, wherein the first graphic comprises a first row of one or more objects and a second row of one or more objects, and wherein one of the one or more objects in the first row represents a first target result that is desired to be accomplished by a breathing motion of the patient;
   displaying a second graphic on the screen, wherein the second graphic represents a breathing state of the patient;
   moving the first graphic in accordance with a predetermined medical plan; and
   moving the second graphic in response to the breathing motion of the patient;
   wherein the one of the one or more objects in the first row comprises a rectangular block that has a first boundary, a second boundary, a third boundary, and a fourth boundary, the first boundary and the second boundary defining a range of positions that define the first target result, the third boundary representing a desired starting time for the first target result, and the fourth boundary representing a desired ending time for the first target result.

17. A system for prompting a patient during a medical procedure, comprising:
   a processor configured to cause a screen that is for viewing by the patient to:
   display a first graphic, wherein the first graphic comprises a first row of one or more objects and a second row of one or more objects, and wherein one of the one or more objects in the first row represents a first target result that is desired to be accomplished by a breathing motion of the patient; and
   display a second graphic, wherein the second graphic represents a breathing state of the patient;
   wherein the processor is further configured to cause the first graphic to move in accordance with a predetermined medical plan, and to move the second graphic in response to the breathing motion of the patient; and
   wherein the first row comprises a first horizontal row, the second row comprises a second horizontal row, and the processor is configured to cause the one or more objects in the first row and the one or more objects in the second row to move horizontally.

18. The system of claim 17, wherein the one of the one or more objects in the first row is associated with a portion of a gantry rotation, and has a length that represents a prescribed duration of a breath-hold.

19. The system of claim 17, wherein the first graphic is moved in synchronization with a movement of a medical device.

20. The system of claim 19, wherein the medical device comprises a radiation source.

21. The system of claim 17, wherein the displayed first and second graphics are configured to allow the patient to decide when to begin the breathing motion in order to accomplish the first target result by a future time.

22. The system of claim 17, wherein the first graphic has a feature representing a range of positions of a radiation source at which radiation will be provided by the radiation source.

23. The system of claim 17, wherein the first and the second graphics are configured to provide an indication to the patient of a relationship among the breathing state of the patient, a desired breathing level to be accomplished, and a future time by which to accomplish the desired breathing level.

24. The system of claim 17, wherein a position of the one of the one or more objects in the first row relative to a reference point indicates a remaining duration before a future time for accomplishing the first target result will arrive.

25. The system of claim 17, wherein the medical procedure comprises an imaging procedure.

26. The system of claim 17, wherein the processor is further configured to change a configuration of the first graphic in response to the patient accomplishing at least part of the first target result.

27. The system of claim 17, wherein another one of the one or more objects in the first row represents a second target result that is desired to be accomplished.

28. The system of claim 17, wherein the one or more objects in the first row and the one or more objects in the second row are arranged in a staggered configuration.

29. The system of claim 17, wherein each of the one or more objects in the first row comprises a rectangular block.

30. A system for prompting a patient during a medical procedure, comprising:
   a processor configured to cause a screen that is for viewing by the patient to:
   display a first graphic, wherein the first graphic comprises a first row of one or more objects and a second row of one or more objects, and wherein one of the one or more objects in the first row represents a first target result that is desired to be accomplished by a breathing motion of the patient; and
   display a second graphic, wherein the second graphic represents a breathing state of the patient;
   wherein the processor is further configured to cause the first graphic to move in accordance with a predetermined medical plan, and to move the second graphic in response to the breathing motion of the patient; and
   wherein the one of the one or more objects in the first row comprises a rectangular block that has a first boundary, a second boundary, a third boundary, and a fourth boundary, the first boundary and the second boundary defining a range of positions that define the first target result, the third boundary representing a desired starting time for the first target result, and the fourth boundary representing a desired ending time for the first target result.

31. A computer product having a set of instruction stored in a non-transitory medium, wherein an execution of the instruction causes a process for prompting a patient during a medical procedure to be performed, the process comprising:
   displaying a first graphic on a screen for viewing by the patient, wherein the first graphic comprises a first row of one or more objects and a second row of one or more objects, and wherein one of the one or more objects in the first row represents a first target result that is desired to be accomplished by a breathing motion of the patient;

displaying a second graphic on the screen, wherein the second graphic represents a breathing state of the patient;

moving the first graphic in accordance with a predetermined medical plan; and moving the second graphic in response to the breathing motion of the patient;

wherein the first row comprises a first horizontal row, the second row comprises a second horizontal row, and the act of moving the first graphic comprises moving the one or more objects in the first row and the one or more objects in the second row horizontally.

32. The computer product of claim 31, wherein the one of the one or more objects in the first row is associated with a portion of a gantry rotation, and has a length that represents a prescribed duration of a breath-hold.

33. The computer product of claim 31, wherein the act of moving the first graphic is performed in synchronization with a movement of a medical device.

34. The computer product of claim 33, wherein the medical device comprises a radiation source.

35. The computer product of claim 31, wherein the displayed first and second graphics are configured to allow the patient to decide when to begin the breathing motion in order to accomplish the first target result by a future time.

36. The computer product of claim 31, wherein the first graphic has a feature representing a range of positions of a radiation source at which radiation will be provided by the radiation source.

37. The computer product of claim 31, wherein the first and the second graphics are configured to provide an indication to the patient of a relationship among the breathing state of the patient, a desired breathing level to be accomplished, and a future time by which to accomplish the desired breathing level.

38. The computer product of claim 31, wherein a position of the one of the one or more objects in the first row relative to a reference point indicates a remaining duration before a future time for accomplishing the first target result will arrive.

39. The computer product of claim 31, wherein the medical procedure comprises an imaging procedure.

40. The computer product of claim 31, further comprising changing a configuration of the first graphic in response to the patient accomplishing at least part of the first target result.

41. The computer product of claim 31, wherein another one of the one or more objects in the first row represents a second target result that is desired to be accomplished.

42. The computer product of claim 31, wherein the one or more objects in the first row and the one or more objects in the second row are arranged in a staggered configuration.

43. The computer product of claim 31, wherein each of the one or more objects in the first row comprises a rectangular block.

44. A computer product having a set of instruction stored in a non-transitory medium, wherein an execution of the instruction causes a process for prompting a patient during a medical procedure to be performed, the process comprising:

displaying a first graphic on a screen for viewing by the patient, wherein the first graphic comprises a first row of one or more objects and a second row of one or more objects, and wherein one of the one or more objects in the first row represents a first target result that is desired to be accomplished by a breathing motion of the patient;

displaying a second graphic on the screen, wherein the second graphic represents a breathing state of the patient;

moving the first graphic in accordance with a predetermined medical plan; and moving the second graphic in response to the breathing motion of the patient;

wherein the one of the one or more objects in the first row comprises a rectangular block that has a first boundary, a second boundary, a third boundary, and a fourth boundary, the first boundary and the second boundary defining a range of positions that define the first target result, the third boundary representing a desired starting time for the first target result, and the fourth boundary representing a desired ending time for the first target result.

* * * * *